US006255499B1

(12) United States Patent
Kuperman et al.

(10) Patent No.: US 6,255,499 B1
(45) Date of Patent: Jul. 3, 2001

(54) PROCESS FOR THE HYDRO-OXIDATION OF OLEFINS TO OLEFIN OXIDES USING OXIDIZED GOLD CATALYST

(75) Inventors: Alex Kuperman; Robert G. Bowman; Howard W. Clark; George E. Hartwell; Brian J. Schoeman; Hendrik E. Tuinstra, all of Midland, MI (US); Garmt R. Meima, Terneuzen (NL)

(73) Assignee: The Dow Chemical Company, Midland, MI (US)

( * ) Notice: Subject to any disclaimer, the term of this patent is extended or adjusted under 35 U.S.C. 154(b) by 0 days.

(21) Appl. No.: 09/544,743

(22) Filed: Apr. 7, 2000

Related U.S. Application Data
(60) Provisional application No. 60/128,394, filed on Apr. 8, 1999.

(51) Int. Cl.[7] .................... C07D 301/04; C07D 301/10; B01J 23/52; B01J 21/06
(52) U.S. Cl. .................... 549/523; 549/532; 549/533; 502/243; 502/344
(58) Field of Search .................... 549/523, 532, 549/533; 502/243, 344

(56) References Cited

U.S. PATENT DOCUMENTS

| | | | |
|---|---|---|---|
| 4,007,135 | 2/1977 | Hayden et al. | 252/467 |
| 4,242,235 | 12/1980 | Cognion et al. | 252/455 |
| 4,391,756 | 7/1983 | Kuch et al. | 260/430 |
| 4,410,501 | 10/1983 | Taramasso et al. | 423/326 |
| 4,701,428 | 10/1987 | Bellussi et al. | 502/8 |
| 4,839,327 | 6/1989 | Haruta et al. | 502/243 |
| 4,845,253 | 7/1989 | Bowman | 549/536 |
| 4,937,219 | 6/1990 | Haruta et al. | 502/174 |
| 5,008,414 | 4/1991 | Ramachandran et al. | 549/538 |
| 5,051,394 | 9/1991 | Haruta et al. | 502/324 |
| 5,162,283 | 11/1992 | Moini | 502/236 |
| 5,354,875 | 10/1994 | Nemeth et al. | 549/531 |
| 5,506,273 | 4/1996 | Haruta et al. | 518/713 |
| 5,703,254 | 12/1997 | Gaffney et al. | 549/536 |
| 5,932,750 | 8/1999 | Hayashi et al. | 549/523 |
| 5,965,754 | 10/1999 | Clark et al. | 549/533 |
| 6,031,116 | 2/2000 | Bowman et al. | 549/523 |

FOREIGN PATENT DOCUMENTS

| | | |
|---|---|---|
| 196 00 709 A1 | 7/1997 | (DE). |
| 0 200 260 A2 | 12/1986 | (EP). |
| 0 568 336 B1 | 11/1993 | (EP). |
| 0 638 362 A1 | 2/1995 | (EP). |
| 0 709 360 A1 | 5/1996 | (EP). |
| 0 723 810 A1 | 7/1996 | (EP). |
| 0 850 936 A1 | 7/1998 | (EP). |
| 0916403 A2 | 5/1999 | (EP). |
| 1 327 497 | 8/1973 | (GB). |
| 1 338 901 | 11/1973 | (GB). |
| 1 409 421 | 10/1975 | (GB). |
| 4-352771 | 12/1992 | (JP). |
| 7-8797 | 1/1995 | (JP). |
| 7-53577 | 6/1995 | (JP). |
| 8-269029 | 10/1996 | (JP). |
| 10-5590 | 1/1998 | (JP). |
| 94/23834 | 10/1994 | (WO). |
| 96/02323 A1 | 2/1996 | (WO). |
| 97/25143 A1 | 7/1997 | (WO). |
| 97/34692 A1 | 9/1997 | (WO). |
| 97/47386 | 12/1997 | (WO). |
| 98/00413 | 1/1998 | (WO). |
| 98/00414 | 1/1998 | (WO). |
| 98/00415 | 1/1998 | (WO). |
| 00/00188 | 1/1999 | (WO). |
| 99/43431 | 9/1999 | (WO). |
| 99/52883 | 10/1999 | (WO). |

OTHER PUBLICATIONS

Haruta, Masatake, "Catalysis of Ultra–fine Gold Particles Deposited on Metal Oxides", Workshop on Environmental Catalysis: The Role of 1B Metals (Nov. 2–3, 1995) Ikeda, Osaka, Japan, pp. 109–118.

Hayashi, Toshio et al., "Selective Partial Oxidation of Hydrocarbons over $Au/TiO_2$ Catalysts", Symposium on Heterogeneous Hydrocarbon Oxidation Presented Before the Division of Petroleum Chemistry, Inc., 211th National Meeting, American Chemical Society, New Orleans, LA (Mar. 24–29, 1996) pp. 71–74.

Kalvachev, Yuri A. et al., "Selective Partial Oxidation of Propylene to Propylene Oxide on Au/Ti–MCM Catalysts in the Presence of Hydrogen and Oxygen", 3rd World Congress on Oxidation Catalysis, R. K. Grasselli et al. (Editors), Elsevier Science B.V. (Pub.) (Sep. 24, 1997) pp. 965–972.

Yen–Shuo Su et al., "XPS and DRS of $Au/TiO_2$ catalysts: effect of pretreatment," *Catalysis Letters*, 57 (1999), 49–53.

M. A. P. Dekkers et al., "CO adsorption and oxidation on $Au/TiO_2$," *Catalysis Letters*, 56, (1998), 195–197.

S. Tsubota et al., Preparation of nanometer gold strongly interacted with $TiO_2$ and the structure sensitivity in lowtemperature oxidation of CO, *Preparation of Catalysts VI: Scientific Bases for the Preparation of Heterogeneous Catalysts*, G Poncelet et al., eds., Elsevier Science B.V., Netherlands, 1995, pp. 227–235.

S. Tsubota et al., "Preparation of Highly Dispersed Gold on Titanium and Magnesium Oxide," Preparation of Catalysts V, G. Poncelet et al., eds., Elsevier Science B.V., Netherlands, 1991, pp. 695–704.

M. Valden et al., "Onset of Catalytic Activity of Gold Clusters on Titania with the Appearance of Nonmetallic Properties," *Science*, 281 (1998), 1647–1650.

*Primary Examiner*—Ba K. Trinh
(74) *Attorney, Agent, or Firm*—Marie F. Zuckerman

(57) ABSTRACT

A process and catalyst for the hydro-oxidation of an olefin having three or more carbon atoms, such as propylene, to form an olefin oxide, such as propylene oxide. The process involves contacting the olefin with oxygen under reaction conditions in the presence of hydrogen and a catalyst. The catalyst contains oxidized gold dispersed on a titanium-containing support, preferably, a support having a plurality of titanium coordination environments, for example, titanium grafted onto a titanosilicate. Selectivity to olefin oxide is high at good conversion of the olefin. The catalyst uses hydrogen efficiently and exhibits a long lifetime.

104 Claims, No Drawings

PROCESS FOR THE HYDRO-OXIDATION OF OLEFINS TO OLEFIN OXIDES USING OXIDIZED GOLD CATALYST

CROSS REFERENCE TO RELATED APPLICATION

This application claims the benefit of U.S. Provisional Application No. 60/128,394, filed Apr. 8, 1999.

BACKGROUND OF THE INVENTION

This invention pertains to a process and catalyst for the hydro-oxidation of olefins, such as propylene, by oxygen in the presence of hydrogen to olefin oxides, such as propylene oxide.

Olefin oxides, such as propylene oxide, are used to alkoxylate alcohols to form polyether polyols, which find significant utility in the manufacture of polyurethanes and synthetic elastomers. Olefin oxides are also important intermediates in the manufacture of alkylene glycols, such as propylene glycol, and alkanolamines, such as isopropanolamine, which are useful as solvents and surfactants.

Propylene oxide is produced commercially via the well-known chlorohydrin process wherein propylene is reacted with an aqueous solution of chlorine to produce a mixture of propylene chlorohydrins. The chlorohydrins are dehydrochlorinated with an excess of alkali to produce propylene oxide. This process suffers from the production of a low concentration salt stream. (See K. Weissermel and H. J. Arpe, *Industrial Organic Chemistry*, $2^{nd}$ ed., VCH Publishers, Inc., New York, N.Y., 1993, pp. 264–265.)

Another well-known route to olefin oxides relies on the transfer of an oxygen atom from an organic hydroperoxide or peroxycarboxylic acid to an olefin. In the first step of this oxidation route, a peroxide generator, such as isobutane, ethylbenzene, or acetaldehyde, is autoxidized with oxygen to form a peroxy compound, such as t-butyl hydroperoxide, ethylbenzene hydroperoxide, or peracetic acid. The peroxide is used to epoxidize the olefin, typically in the presence of a transition metal catalyst, including titanium, vanadium, molybdenum, and other metal compounds or complexes. Along with the olefin oxide produced, this process disadvantageously produces equimolar amounts of a coproduct, for example, an alcohol, such as t-butanol or methylphenylcarbinol, or an acid, such as acetic acid. Coproducts such as t-butanol and acetic acid must be recycled or their value must be captured in the market place. Other coproducts must be further processed into products of commercial value; for example, methylphenylcarbinol must be dehydrated to form styrene. (*Industrial Organic Chemistry*, ibid., pp. 265–269.)

More recently, the direct oxidation of olefins, such as propylene, with oxygen in the presence of hydrogen and a catalyst has been reported to yield olefin oxides, such as propylene oxide, as illustrated in EP-A1 -0,709,360. It is taught that the catalyst comprises ultrafine particles of metallic gold deposited on titanium dioxide, preferably, the crystalline anatase phase. This catalyst exhibits a disadvantageously short lifetime. Moreover, when operated at temperatures of greater than about 100° C., the catalyst exhibits low olefin oxide selectivity and high water production.

Other hydro-oxidation processes are known, for example, as described in international patent publications WO 98/00413 and WO 98/00415, wherein an olefin, such as propylene, is reacted with oxygen in the presence of hydrogen and a catalyst comprising gold deposited on a titano-silicate support or gold deposited on a support comprising a disorganized phase of titanium dispersed on silica. International patent publication WO 98/00414 describes a similar process wherein the catalyst comprises gold and a promoter metal, such as a Group 1, Group 2, or lanthanide rare earth metal, deposited on a titanium-containing support. The catalysts of these references achieve better lifetime and better hydrogen efficiency at comparable olefin selectivity when compared with the catalyst of EP-A1-0,709,360. The catalyst of WO 98/00414 also exhibits higher activity than the catalyst of EP-A1-0,709,360. Nevertheless, improvements in activity, lifetime, and hydrogen efficiency are still desirable.

SUMMARY OF THE INVENTION

This invention is a novel hydro-oxidation process of preparing an olefin oxide directly from an olefin and oxygen in the presence of hydrogen. The process comprises contacting an olefin having three or more carbon atoms with oxygen in the presence of hydrogen and in the presence of a catalyst under process conditions sufficient to produce the corresponding olefin oxide. The unique catalyst which is employed in the process of this invention comprises oxidized gold dispersed on a titanium-containing support. The words "oxidized gold" mean that the gold is present as non-metallic gold, that is, gold in one or more positive oxidation state(s) of greater than 0. Any modern analytical method (for example, X-ray photoelectron spectroscopy) or combination of analytical methods that can determine the presence of oxidized gold can be suitably employed.

The novel process of this invention is useful for producing an olefin oxide directly from oxygen and an olefin having three or more carbon atoms. Unexpectedly, the process of this invention produces the olefin oxide at high operating temperatures and over a sustained period of time with high activity and high selectivity. Partial and complete combustion products, such as acrolein and carbon dioxide, are produced in low amounts in the process of this invention. Significantly, the process of this invention can be operated at higher temperatures than prior art processes, specifically, temperatures from greater than about 130° C. up to about 300° C. Operation at higher temperatures advantageously provides steam credits from the heat produced. Accordingly, the process of this invention can be integrated into a total plant design wherein the heat derived from the steam is used to drive additional processes, for example, the separation of the olefin oxide from water, the latter being produced as a co-product of the hydro-oxidation process. Even more advantageously, in preferred embodiments of the process of this invention, the hydrogen efficiency, as measured by the molar ratio of water to olefin oxide produced, is significantly improved when compared with processes of the prior art. In preferred embodiments, for example, a water to olefin oxide molar ratio of less than about 10:1 can be achieved over sustained periods of time at high operating temperatures. Even more advantageously, in preferred embodiments, the process achieves improved olefin conversion with little deactivation over a period of at least about 100 hours. Most advantageously, the process can be conducted using lower gold loadings than those used in prior art processes.

In another aspect, this invention is a unique catalyst composition comprising oxidized gold dispersed on a titanium-containing support. As noted hereinbefore, the oxidized gold comprises non-metallic gold, that is, gold characterized by one or more oxidation states greater than 0.

The novel composition of this invention can be effectively used in the aforementioned hydro-oxidation process wherein an olefin having three or more carbon atoms is converted to the corresponding olefin oxide. Besides being active and highly selective for the olefin oxide, in preferred embodiments, the novel catalyst of this invention utilizes hydrogen more efficiently and exhibits a significantly longer lifetime, as compared with catalysts of the prior art. Moreover, the catalyst of this invention achieves this high performance level at operating temperatures which are higher than those used in prior art processes. Operation at higher temperatures results in useful steam credits for running associated or downstream processes. As an added advantage, the catalyst of this invention can be operated with lower gold loadings than those used in prior art processes. A lower gold loading provides advantageous economic benefits. Accordingly, this unique catalyst possesses highly desirable properties for the process of oxidizing propylene and higher olefins to their corresponding olefin oxides.

In one preferred embodiment, the catalyst of this invention can be advantageously prepared by an impregnation technique that greatly simplifies commercial preparation, as compared with the prior art preparation method involving deposition-precipitation. The impregnation method advantageously avoids the handling of large volumes of gold-containing solutions and the need for carefully controlling pH.

DETAILED DESCRIPTION OF THE INVENTION

The novel hydro-oxidation process of this invention comprises contacting an olefin having three or more carbon atoms with oxygen in the presence of hydrogen and an epoxidation catalyst under process conditions sufficient to prepare the corresponding olefin oxide. Optionally, a diluent may be employed in the process. The relative molar quantities of olefin, oxygen, hydrogen, and optional diluent can be any which are sufficient to prepare the desired olefin oxide. In a preferred embodiment of this invention, the olefin is a $C_{3-12}$ olefin, and it is converted to the corresponding $C_{3-12}$ olefin oxide. In a more preferred embodiment, the olefin employed is a $C_{3-8}$ olefin, and it is converted to the corresponding $C_{3-8}$ olefin oxide. In a most preferred embodiment, the olefin is propylene, and the olefin oxide is propylene oxide.

The novel catalyst which is employed in the epoxidation process of this invention comprises oxidized gold dispersed on a titanium-containing support. The oxidized gold is characterized as having a positive oxidation state, or combination of positive oxidation states, greater than 0. In other words, the oxidized gold is non-metallic gold. One skilled in the art will recognize that metallic gold (or elemental gold) has an oxidation state of 0.

In a preferred embodiment, the titanium-containing support comprises titanium grafted onto a titanosilicate, as described in detail hereinafter. In another preferred embodiment, the titanium-containing support comprises titanium dispersed on a support, prepared by a method comprising dispersing a titanium-containing monomer, dimer, polymer, or mixture thereof onto a support. In another preferred embodiment, the titanium-containing support comprises titanium dispersed on silica, prepared by a method comprising dispersing a titanium-silicon oxide monomer, dimer, polymer, or mixture thereof onto a support. In one preferred embodiment, the catalyst of this invention excludes oxidized gold deposited on bulk titanium dioxide.

In yet another preferred embodiment, the catalyst further comprises a promoter metal which is defined as any metal or metallic ion which enhances the performance of the catalyst. More preferably, the promoter metal is selected from silver, Group 1, Group 2, the lanthanide rare earth and actinides elements of the Periodic Table, as referenced in the *CRC Handbook of Chemistry and Physics*, 75$^{th}$ ed., CRC Press, 1994. In yet another preferred embodiment, the titanium-containing support is prepared by a method comprising dispersing a mixture containing a promoter metal alkoxide and a titanium alkoxide on silica.

Any olefin containing three or more carbon atoms or mixture of such olefins can be employed in the process of this invention. Monoolefins are suitable, as are compounds containing two or more olefinic bonds, such as dienes. The olefin can be a simple hydrocarbon containing only carbon and hydrogen atoms; or alternatively, the olefin can be substituted at any of the carbon atoms with an inert substituent. The term "inert", as used herein, requires the substituent to be substantially non-reactive in the process of this invention. Suitable inert substituents include, but are not limited to, halides, ether, ester, alcohol, and aromatic moieties; preferably, chloro, $C_{1-12}$ ether, $C_{1-12}$ ester, and $C_{1-12}$ alcohol moieties, and $C_{6-12}$ aromatic moieties. Non-limiting examples of olefins which are suitable for the process of this invention include propylene, 1-butene, 2-butene, 2-methylpropene, 1-pentene, 2-pentene, 2-methyl-1-butene, 2-methyl-2-butene, 1-hexene, 2-hexene, 3-hexene, and analogously, the various isomers of methylpentene, ethylbutene, heptene, methylhexene, ethylpentene, propylbutene, the octenes, including preferably 1-octene, and other higher analogues of these; as well as butadiene, cyclopentadiene, dicyclopentadiene, styrene, α-methylstyrene, divinylbenzene, allyl alcohol, allyl ether, allyl ethyl ether, allyl butyrate, allyl acetate, allyl benzene, allyl phenyl ether, allyl propyl ether, and allyl anisole. Preferably, the olefin is an unsubstituted or substituted $C_{3-12}$ olefin, more preferably, an unsubstituted or substituted $C_{3-8}$ olefin. Most preferably, the olefin is propylene. Many of the aforementioned olefins are available commercially; others can be prepared by chemical processes known to those skilled in the art.

The quantity of olefin employed can vary over a wide range provided that the corresponding olefin oxide is produced in the process. Generally, the quantity of olefin depends upon the specific process features, including for example, the design of the reactor, the specific olefin, and economic and safety considerations. Those skilled in the art will know how to determine a suitable range of olefin concentrations for the specific process features. In light of the disclosure herein, the quantity of olefin is typically greater than about 1, preferably, greater than about 10, and more preferably, greater than about 20 mole percent, based on the total moles of olefin, oxygen, hydrogen, and optional diluent. Typically, the quantity of olefin is less than about 99, preferably, less than about 85, and more preferably, less than about 70 mole percent, based on the total moles of olefin, oxygen, hydrogen, and optional diluent.

Oxygen is also required for the process of this invention. Any source of oxygen is acceptable, including air or essentially pure molecular oxygen. Other sources of oxygen may be suitable, including ozone and nitrogen oxides, such as nitrous oxide. Molecular oxygen is preferred. The quantity of oxygen employed can vary over a wide range provided that the quantity is sufficient for producing the desired olefin oxide. Ordinarily, the number of moles of oxygen per mole of olefin used in the feedstream is less than 1. Preferably, the quantity of oxygen is greater than about 0.01, more preferably, greater than about 1, and most preferably greater than about 5 mole percent, based on the total moles of olefin, hydrogen, oxygen, and optional diluent. Preferably, the quantity of oxygen is less than about 30, more preferably, less than about 25, and most preferably less than about 20 mole percent, based on the total moles of olefin, hydrogen, oxygen, and optional diluent. Above about 20 mole percent, the concentration of oxygen may fall within the flammable range for olefin-hydrogen-oxygen mixtures.

Hydrogen is also required for the process of this invention. In the absence of hydrogen, the activity of the catalyst is significantly decreased. Any source of hydrogen can be used in the process of this invention, including for example, molecular hydrogen obtained from the dehydrogenation of hydrocarbons and alcohols. In an alternative embodiment of this invention, the hydrogen may be generated in situ in the olefin oxidation reactor, for example, by dehydrogenating alkanes, such as propane or isobutane, or alcohols, such as isobutanol. Alternatively, hydrogen may be used to generate a catalyst-hydride complex or a catalyst-hydrogen complex which can provide the necessary hydrogen to the process.

Any quantity of hydrogen can be employed in the process provided that the amount is sufficient to produce the olefin oxide. Suitable quantities of hydrogen are typically greater than about 0.01, preferably, greater than about 0.1, and more preferably, greater than about 3 mole percent, based on the total moles of olefin, hydrogen, oxygen, and optional diluent. Suitable quantities of hydrogen are typically less than about 50, preferably, less than about 30, and more preferably, less than about 20 mole percent, based on the total moles of olefin, hydrogen, oxygen, and optional diluent.

In addition to the above reagents, it may be desirable to employ a diluent with the reactants, although the use thereof is optional. Since the process of this invention is exothermic, a diluent beneficially provides a means of removing and dissipating the heat produced. In addition, the diluent provides an expanded concentration regime in which the reactants are non-flammable. The diluent can be any gas or liquid which does not inhibit the process of this invention. The specific diluent chosen will depend upon the manner in which the process is conducted. For example, if the process is conducted in a gas phase, then suitable gaseous diluents include, but are not limited to, helium, nitrogen, argon, methane, carbon dioxide, steam, and mixtures thereof. Most of these gases are essentially inert with respect to the process of this invention. If the process is conducted in a liquid phase, then the diluent can be any oxidation stable and thermally stable liquid. Examples of suitable liquid diluents include aliphatic alcohols, preferably $C_{1-10}$ aliphatic alcohols, such as methanol and t-butanol; chlorinated aliphatic alcohols, preferably $C_{1-10}$ chlorinated alkanols, such as chloropropanol; chlorinated hydrocarbons, preferably $C_{1-10}$ chlorinated hydrocarbons, such as dichloroethane and chlorinated benzenes, including chlorobenzene and dichlorobenzene; aromatic hydrocarbons, preferably, $C_{6-15}$ aromatic hydrocarbons, such as benzene, toluene, and xylenes; ethers, preferably, $C_{2-20}$ ethers, including tetrahydrofuran and dioxane; as well as liquid polyethers, polyesters, and polyalcohols.

If a diluent is used in the gas phase, the amount of diluent is typically greater than about 0, preferably greater than about 0.1, and more preferably, greater than about 15 mole percent, based on the total moles of olefin, oxygen, hydrogen, and diluent. If a diluent is used in the gas phase, the amount of diluent is typically less than about 90, preferably, less than about 80, and more preferably, less than about 70 mole percent, based on the total moles of olefin, oxygen, hydrogen, and diluent. If a liquid diluent (or solvent) is used in the liquid phase, the amount of liquid diluent (or solvent) is typically greater than about 0, and preferably, greater than about 5 weight percent, based on the total weight of the olefin and diluent. If a liquid diluent is used in the liquid phase, the amount of liquid diluent is typically less than about 99, and preferably, less than about 95 weight percent, based on the total moles of olefin and diluent.

The concentrations of olefin, oxygen, hydrogen, and diluent disclosed hereinabove are suitably based on the reactor designs and process parameters disclosed herein. Those skilled in the art will recognize that concentrations other than those disclosed herein may be suitably employed in other various engineering realizations of the process.

The unique catalyst which is beneficially employed in the hydro-oxidation process of this invention comprises gold on a titanium-containing support, characterized in that gold is present as oxidized gold, or in equivalent words, non-metallic gold. Oxidized gold is defined as any gold specie(s) having an oxidation state or combination of oxidation states greater than 0. Any modem analytical technique which can determine the gold oxidation state(s) or their relative amounts can be employed, including, for example, X-ray photoelectron spectroscopy (XPS). XPS data can be collected on a Kratos Axis 165 XPS instrument or a PHI 5400 XPS instrument using the features and conditions noted hereinafter, or any equivalent instrument thereof. In some embodiments of the catalyst, particularly those wherein organic ligands are present, X-rays may induce reduction of a portion of the oxidized gold. Under these circumstances, the percentage of oxidized gold measured by XPS may be lower than the actual percentage in the catalyst. In addition to XPS, high resolution transmission electron spectroscopy (HR-TEM) can be employed to analyze for the presence or absence of metallic gold particles. Any high resolution transmission electron microscope having a point to point resolution of 2 Å or higher resolution can be employed for this purpose. Mie scattering, measured on an ultraviolet-visible diffuse reflectance spectrometer (UV-VIS DRS), for example, a DRS Model UV- 3101 PC scanning through the 525 nm region, can also be employed to analyze for the presence or absence of metallic gold. When the catalyst is essentially white or faintly colored, essentially no peak above background is observed in the Mie scattering region, or at most, a very weak peak may be observed. These observations are consistent with the absence or near-absence of metallic gold. A gold elemental analysis can confirm the presence of gold and, by implication, oxidized gold when other techniques do not reveal the presence of metallic gold particles. Preferably, the gold oxidation state ranges from greater than 0 to about +3. In contrast, metallic gold has an oxidation state of 0.

Typically, the oxidized gold comprises greater than about 30 percent by weight of the total gold content. Preferably, the oxidized gold comprises greater than about 50 percent, and more preferably, greater then about 70 percent by weight of the total gold content. In one of the most preferred embodiments, the catalyst comprises essentially oxidized gold, which means that greater than about 90 percent by weight of the total gold content is oxidized. In another most preferred embodiment, the catalyst comprises greater than about 95 weight percent oxidized gold.

If metallic gold is present, no limitation is placed on its absolute amount or particle size; however, the typical and preferred quantities of oxidized gold relative to metallic gold have been noted hereinbefore. Typically, the average size of metallic gold particles, when they are present, is less than about 150 nm, even more typically, less than about 50 nm, as measured by HR-TEM. In a preferred embodiment, essentially no metallic gold is present, which appears to correlate with better hydrogen efficiency (low water to olefin oxide molar ratio) in the hydro-oxidation process. When the catalyst contains essentially no metallic gold and the support is white, the catalyst is typically white or has a faint color.

The gold loading on the support can be any amount which yields an active catalyst in the process of this invention. Generally, the gold loading is greater than about 0.001 weight percent (10 parts per million), preferably, greater than about 0.005, and more preferably, greater than about 0.01 weight percent, based on the total weight of the catalyst. Generally, the gold loading is less than about 20, preferably, less than about 10, and more preferably, less than about 5.0 weight percent, based on the total weight of the catalyst. In one preferred embodiment, the process is advantageously conducted at a gold loading of less than about 0.5 weight percent, more preferably, less than about 0.1 weight percent.

The titanium-containing support may take a variety of forms. Preferably, the titanium in the support exists essentially as non-metallic titanium. The support, itself, can be any material, for example, to which titanium can be affixed including amorphous or crystalline silicas, such as silicalite or MCM-41; aluminas; metallosilicates, such as, aluminosilicates and titanosilicates; promoter metal silicates, such as, the silicates of Groups 1 and 2, and the lanthanide and actinide elements; and other refractory oxides and like support materials. Still other titanium-containing supports which are suitable for the hydro-oxidation process of this invention include porous crystalline titanosilicates of the prior art, such as TS-1, TS-2, Ti-beta, Ti-MCM-41, and Ti-MCM-48, as well as, stoichiometric and non-stoichiometric promoter metal titanates. The promoter metal titanates can also be crystalline or amorphous. Non-limiting examples of these include the titanates of Group 1, Group 2, and the lanthanide and actinide metals. Preferably, the promoter metal titanate is selected from the group consisting of magnesium titanate, calcium titanate, barium titanates, strontium titanate, sodium titanate, potassium titanate, and the titanates of erbium, lutetium, thorium, and uranium. As a further alternative, amorphous and crystalline titanium oxides, including the anatase, rutile, and brookite phases of titanium dioxide, can be suitably employed as the titanium-containing support.

The titanium-containing support may be crystalline, quasi-crystalline, or amorphous, and may contain a regular or irregular arrangement of non-connecting or interconnecting micropores and/or mesopores. As used herein, the term "micropore" implies a pore diameter (or critical dimension as in the case of a non-circular perpendicular cross-section) ranging from about 4 Å to about 20 Å, while the term "mesopore" implies a pore diameter or critical dimension ranging from greater than about 20 Å to about 500 Å.

In those instances wherein titanium is affixed to the support, the titanium loading can be any which gives rise to an active catalyst in the process of this invention. Typically, the titanium loading is greater than about 0.02 weight percent, preferably, greater than about 0.1 weight percent, based on the weight of the support. Typically, the titanium loading is less than about 20 weight percent, and preferably, less than about weight percent, based on the weight of the support.

In one preferred embodiment, the titanium-containing support possesses a plurality (two or more) of titanium coordination environments, resulting in a plurality of titanium species. The coordination environment relates to the number of bonds and the geometry of the bonds to titanium. As applied to titanosilicates, the coordination environments can include framework and non-framework titanium. By way of explanation, a crystalline titanosilicate possesses a three-dimensional structure, known as a "framework," constructed from $SiO_4$ tetrahedra, wherein each oxygen atom bridges two silicon atoms. A framework titanium is defined as a titanium atom which has replaced a framework silicon. In contrast, non-framework titanium is defined as a titanium atom/ion which is connected to the framework typically through an oxygen bridge. There is no limitation on the manner in which the non-framework titanium is bonded onto the framework. Any type of bonding ranging from very weak interactions (weak Coulombic interactions) to fully coordinated (anchored or grafted) bonds, are acceptable. Thus, deposited, dispersed, and grafted models are contemplated. A full description of suitable metal-support interactions can be found in B. Delmon in "Preparation of Solid Catalysts," *Handbook of Heterogeneous Catalysis*, Vol. 2, G. Ertl, H. Knözinger, and J. Weitkamp, eds., VCH Verlagsgesellschaft mbH, Weinheim, Germany, 1997, pp. 264–286, incorporated herein by reference. In another aspect, the titanium in this preferred support, whether framework or non-framework titanium, is not limited to any particular site coordination, so long as there are a plurality of coordination sites. Coordinations, such as tetrahedral, trigonal bipyramidal, square pyramidal, octahedral, and distorted variations thereof are all acceptable. The plurality of coordination types may also be satisfied by having two or more variations of the same coordination, for example, two different types of tetrahedral coordination, as determined by analytical techniques described hereinafter. Non-limiting examples of supports containing non-framework and, optionally, framework titanium include titania (or other discrete titanium-containing compositions) occluded onto a support material, such as, a silicate or metallosilicate (for example, titanosilicate) framework; titanium deposited as ions or ion clusters onto a support material, such as, a refractory oxide or a metallosilicate (for example, titanosilicate) framework; and titanium, preferably non-metallic titanium, grafted onto a framework structure, such as titanium grafted onto a silicate or titanosilicate framework.

A novel modified titanosilicate has now been discovered which is a more preferred titanium-containing support for the process of this invention. This modified titanosilicate comprises a quasi-crystalline material with an MFI structure, as determined by X-ray diffraction (XRD), and possesses a plurality of titanium species, as determined, for example, by XPS and/or US-VIS DRS. At least one titanium species is believed to be a framework titanium; at least one of the other titanium species is believed to be a grafted titanium, although this theory should not limit the composition or process of this invention in any way.

The silicon to titanium atomic ratio (Si:Ti) of the titanosilicate support can be any ratio which provides for an active and selective epoxidation catalyst in the process of this invention. A generally advantageous Si:Ti atomic ratio is equal to or greater than about 5:1, preferably, equal to or greater than about 10:1. A generally advantageous Si:Ti atomic ratio is equal to or less than about 500:1, preferably, equal to or less than about 100:1.

The synthesis of the novel modified titanosilicate is similar, in some aspects, to the preparation of TS-1, which is described in U.S. Pat. No. 4,410,501 and by J. Thangaraj et al. (*Journal of Catalysis*, 130, 1991, pg. 1); but in contrast to the prior art, the synthesis produces a titanosilicate with two or more titanium species. Along similar lines, the reaction mixture comprises water, a source of titanium, a source of silica, and a template in the form of an amine or a quaternary ammonium compound. Almost any source of silica is suitable, including tetraalkylorthosilicates, preferably, tetraethylorthosilicate, or simply fumed or precipitated silicas, but preferably, not a silica containing sodium ions. The source of titanium is any hydrolysable titanium compound, chosen preferably from titanium tetra (alkoxide)s, more preferably, titanium tetra(ethoxide), titanium tetra(n-butoxide), or titanium tetra(isopropoxide); and from titanium tetrahalides, preferably, titanium tetrachloride; and from titanium oxyhalides, such as titanium oxychloride. Another source of the titanium and silica can be mixed titanium and silica composites, such as titanium or titania supported on silica, or silica and titania co-gels. The trialkylamine is preferably a tri($C_{1-15}$ alkyl)amine, such as, triethylamine, tripropylamine, and tri(n-butyl)amine. The quaternary ammonium compound can be a tetraalkylammonium hydroxide or tetraalkylammonium halide, such as, tetra(ethyl)ammonium hydroxide, tetra(propyl)ammonium hydroxide, tetra(n-butyl)ammonium hydroxide, and the corresponding halides, and the like. In the reaction mixture, the molar ratio of silica to titanium can range from about 1:1 to about 1,000:1, preferably, from about 10:1 to about 200:1, and more preferably, from about 20:1 to about 150:1. The molar ratio of water to silica can range from about 15:1 to about 500:1, preferably, from about 20:1 to about 200:1, and more preferably, from about 30:1 to about 100:1. The molar ratio of amine or quaternary ammonium template to silica can range from about 0.1:1 to about 4:1, and preferably, from about 0.4:1 to about 1.0:1. In a preferred synthesis, the source of silica and the source of titanium are mixed, and the resulting mixture is cooled to a temperature between about 0° C. and −6° C., preferably about −4° C. The cooled mixture is then added rapidly, and typically without agitation, to a similarly cooled solution containing the template. The temperature of the resulting synthesis mixture is then raised, and the synthesis is allowed to proceed under hydrothermal conditions, more specifically, in an autoclave at a temperature between about 110° C. and about 220° C. under autogenous pressure for a time ranging from about 1 day to about 10 days. Alternatively, the synthesis may be conducted at atmospheric pressure and at a lower temperature, preferably between about 70° C. up to about 110° C., for a time ranging from about 1 to about 20 days.

In one method of recovery of the novel titanosilicate, the synthesis mixture is ultra-centrifuged to yield a solid, which may be rinsed and dried, for example, freeze dried, to obtain the novel titanosilicate product. In another suitable recovery method, the synthesis mixture is centrifuged, and the liquor obtained from the centrifugation is heated at a temperature between about 50° C. and about 110° C. to rid the liquor of volatile compounds, such as alcohol and amine. Thereafter, the resulting liquor is treated with acid, such as, nitric or hydrochloric acid (from about 0.01 M to about 5.0 M), until precipitation begins. The liquor is then recentrifuged to collect the novel titanosilicate product. In a third recovery method, the aqueous suspension of the novel titanosilicate product can be treated with inorganic acid to adjust the pH to between about 7 and about 9; and thereafter, the acid-treated mixture is centrifuged to collect the titanosilicate product. A fourth recovery method involves centrifuging the synthesis mixture to collect a crystalline solid, which is thereafter washed with acid, for example, about 0.01 M to 5.0 M nitric or hydrochloric acid. The washing, which can be repeated, is generally conducted at a temperature between about 23° C. and about 90° C. The solid product collected by any of these recovery processes is typically dried at a temperature between about ambient, taken as about 21° C., and about 110° C., and then calcined under air at a temperature between about 480° C. and about 750° C. for about 2 to about 12 hours to yield the novel modified titanosilicate support of this invention.

The novel titanosilicate, prepared as described hereinabove, possesses an orthorhombic structure of the MFI structure type, as determined by powder XRD. In contrast to some known TS-1 materials, the novel titanosilicate contains a plurality of titanium species, as determined, for example, by XPS. One XPS peak occurs at about 460 eV, this titanium being a low coordinate or framework species. A second XPS peak occurs at about 458 eV and is assigned to a higher coordinate, non-framework titanium species. The second species does not appear to be crystalline titanium dioxide, since typically X-ray diffraction analysis does not indicate the presence of bulk crystalline titanium dioxide in the material. Alternatively, the titanium species or coordination environments can be analyzed by UV-VIS DRS. By this method, one peak occurs at about 255 nm and is assigned to a framework or low coordinate titanium. At least one other peak is found at greater than about 270 nm and is assigned to a high coordinate, non-framework titanium. The second titanium species is believed to be a form of titanium which is grafted onto the MFI framework; however, such a theory should not be binding upon the invention in any manner. A wide ratio of framework to non-framework (or grafted) titanium species is acceptable. Typically, the ratio of framework to non-framework titanium species can vary from about 95 mole percent framework to about 95 mole percent non-framework. Other titanium species of the framework and/or non-framework types may also be present. The average crystal size of the novel material typically ranges from about 20 nanometers (nm) to about 1 micron ($\mu$m).

Another preferred type of titanium-containing support comprises a disorganized phase of titanium dispersed on a support material, preferably, silica. The disorganized phase of titanium does not exhibit an organized, periodic crystallinity and can be distinguished from a bulk organized (crystalline) phase, such as crystalline titanium dioxide, by one or more modem analytical techniques, such as, HR-TEM, XRD, and Raman spectroscopy. UV-VIS DRS and titanium K edge X-ray absorption near edge structure spectroscopy (XANES) may also be useful in distinguishing the disorganized phase from an organized or crystalline phase. A preferred support containing a disorganized titanium phase is described in international patent publication WO 98/00415, incorporated herein by reference. More preferably, the disorganized titanium phase also contains a plurality of titanium coordination environments as determined, for example, by XPS and/or UV-VIS DRS.

In the preparation of the support comprising disorganized titanium, generally, the starting support is impregnated with a titanium compound at a temperature between about 0° C. and about 50° C., at about ambient pressure, for a time ranging from about 30 minutes to about 24 hours. Non-limiting examples of suitable titanium compounds include titanium alkoxides, such as titanium isopropoxide, titanium propoxide, titanium ethoxide, and titanium butoxide; titanium sulfate, titanium oxysulfate, titanium halides, preferably titanium chloride; titanium carboxylates, preferably titanium oxalate and titanyl acetylacetonate; and organotitanium halides, such as dicyclopentadiene titanium dichloride, and other organotitanocene dichlorides. Mixtures of titanium alkoxides and promoter metal alkoxides, preferably, alkaline earth alkoxides, for example, barium alkoxide, can also be employed. Mixtures of titanium alkoxides and promoter metal alkoxides dissolved in a solvent, such as alcohol, can be obtained commercially, for example, from Gelest, Inc., and deposited together onto the silica. For the mixed alkoxides, the amounts of titanium and promoter alkoxides can be varied in the solution; thus the atomic or weight ratio of promoter to titanium can be varied, as desired. Alternatively, mixed titanium-promoter metal complexes, such as Li[Ti(O—$^i$Bu)$_4$], can be deposited onto the silica. In these true mixed complexes, the amounts of promoter and titanium are fixed, and the ratio of promoter to titanium is not variable.

Other titanium compounds which are suitably employed to prepare the disorganized titanium phase include inorganic and organic titanium-containing monomers, dimers, and polymers, as well as carbon-based polymers functionalized with moieties, such as alkoxides, bound to titanium ions, available commercially, for example, from Gelest, Inc. Non-limiting examples of suitable carbon-based titanium-containing polymers include poly(dibutyltitanate) and poly (octyleneglycol-titanate).

Preferably, the titanium compounds which are suitably employed to prepare the disorganized titanium phase include inorganic and organic titanium and silicon containing monomers, dimers, and polymers, more preferably, titanium and silicon oxide containing monomers, dimers, and polymers. Such materials are well known in the art. The organic titanium monomer, dimer, or polymer may be any compound characterized by a backbone comprised of Si, Ti, and —(CR$_2$)$_z$— moieties, wherein the —(CR$_2$)$_x$— groups are bridging adjoining Si atoms, Ti atoms, or Si and Ti atoms (for example, —Si—(CR$_2$)$_z$—Si—, —Ti—(CR$_2$)$_z$—Ti—, and —Si—(CR$_2$)$_z$—Ti—), and wherein z is an integer ranging from 1 to about 20, and each R is independently selected from alkyl, aryl, alkoxy, and halide groups, preferably, C$_{1-20}$ alkyl, C$_{6-20}$ aryl, C$_{1-20}$ alkoxy, and chloro groups. Pendent to the Si and Ti atoms are organic groups, which preferably take the form of lower alkyl and/or alkoxide groups and/or aryl and/or aryloxide groups. Likewise, the titanosiloxane polymer may be any polymer characterized by a backbone comprised of Si, Ti, and O atoms. The oxygen atoms are bridging adjoining Si atoms, Ti atoms, and Si and Ti atoms (for example, —Si—O—Si—, —Ti—O—Ti—, and —Si—O—Ti—). Pendent to the Si and Ti atoms are organic groups, which preferably take the form of lower alkyl and/or alkoxide groups and/or aryl and/or aryloxide groups. The titanosiloxane polymer may be linear, branched, or cross-linked in structure, the titanium being partially cross-linked with the silicon through Si—O—Ti—O—Si bonding. Titanosiloxane polymers, such as those described in U.S. Pat. No. 5,759,945 (incorporated herein by reference), are particularly suitable. The titanium-containing polymers, such as the titanosiloxanes, can be obtained commercially, for example, from Gelest, Inc. Mixed Ti and Si-containing polymers having both —O— and —(CR$_2$)$_z$— groups in the backbone may also be suitably employed.

More preferably, the aforementioned titanium-containing monomers may be represented by the following formula:

$$(R^1)_x Ti[O—Si(R^2)_{3-y}(R^3)_y]_{4-x}$$

wherein R$^1$, R$^2$, and R$^3$ are each independently selected from the group consisting of alkyl, alkoxy, aryl, aryloxy, and halo moieties, preferably, C$_{1-20}$ alkyl, C$_{1-20}$ alkoxy, C$_{6-20}$ aryl, C$_{6-20}$ aryloxy, and chloro moieties; x is an integer ranging from 0 to 3; and y is an integer ranging from 0 to 3. Likewise, the preferred titanium-containing dimers and polymers may be represented by the formula shown hereinabove, with the exception that R$^3$ can also be selected from the following moieties:

$$[O—Si(R^2)_{3-y}(R^3)_y] \text{ and } [O—Ti(R^2)_{3-y}(R^3)_y]$$

wherein R$^2$, R$^3$, and y can be selected from all of the definitions set forth hereinbefore. Note that R$^3$ is the repeating group. If R$^3$ is repeated once, the formula represents the dimer; if R$^3$ is repeated two or more times, the formula represents the polymer. Non-limiting examples of suitable titanium-containing monomers include tetrakis (trimethylsiloxy)titanium, tetrakis(triethylsiloxy)titanium, tetrakis(triethoxysiloxy)titanium, tetrakis[tris(tert-butoxy)siloxy]titanium, and the like. Non-limiting examples of suitable titanium-containing polymers include diethoxysiloxane-ethyltitanate copolymer.

Other titanium-containing compounds which can be suitably impregnated onto a support to form a disorganized titanium phase include titanium silsesquioxane complexes disclosed by M. Crocker et al. in *Chemical Communications*, 1997, pp. 2411–2412, and by M. Crocker et al. in U.S. Pat. No. 5,750,741, incorporated herein by reference. Additionally, mixtures of any of the aforementioned titanium-containing compounds, complexes, monomers, dimers, and polymers may also be beneficially impregnated onto the support and may be even more preferred for providing a plurality of titanium coordination environments.

The titanium compound can be applied neat, from the gas phase, or from a solvent onto the support of interest. If a solvent is used, it can be any which solubilizes the titanium compound including, for example, aliphatic alcohols, aliphatic and aromatic hydrocarbons, and water where appropriate. After contacting the starting support with the solution containing the titanium compound, the support is dried at a temperature between about 0° C. and about 150° C., preferably between about 50° C. and about 150° C., in a vacuum or in a stream of air or an inert gas, such as nitrogen, argon, or helium. Thereafter, the support can be used without cacination or further treatment. Alternatively after drying, the support can be calcined in air or an inert gas, such as nitrogen or helium, to a temperature between about 100° C. and about 1000° C., preferably between about 100° C. and about 800° C.

Any combination or mixture of titanium-containing supports described hereinabove can be employed in the catalyst of this invention.

The titanium-containing support may be shaped into any form suitable for catalyst particles, for example, beads, pellets, spheres, honeycombs, monoliths, extrudates, and films. Optionally, the titanium-containing support can be extruded with, bound to, or supported on a second support for the purpose of binding together the catalyst particles and/or improving the catalyst's strength or attrition resistance. For example, it may be desirable to prepare a thin film of the titanium-containing support on a secondary support which is shaped into a bead, pellet, or extrudate. The second support is typically inert in the process and need not contain titanium. Suitable secondary supports include carbon and any refractory oxide, such as, silica, alumina, aluminosilicates; ceramics, including ceramic carbides and nitrides, as well as any metallic support. Generally, the quantity of second support ranges from about 0 to about 95 weight percent, based on the combined weight of the catalyst and second support.

There is no limitation on the method of incorporating oxidized gold onto the titanium-containing support, so long as the catalyst produced exhibits activity in the hydro-oxidation process of this invention. Non-limiting examples of suitable preparation methods include deposition-precipitation, impregnation, spray-drying, ion-exchange, vapor deposition, and solid-solid reaction. Deposition-precipitation and impregnation are somewhat preferred. Throughout the preparation, conditions are typically chosen to minimize the reduction of oxidized gold to metallic gold. In the deposition-precipitation method the titanium-containing support is usually contacted with a solution containing a gold compound at a temperature and pH sufficient to incorporate an oxidized gold compound onto the support. The synthesis conditions can be varied as a function of several parameters, for example, the specific nature of the gold compound, the concentration of the gold compound in the solution, the nature and concentration of other ionic species, such as, chloride, sodium ions, and silicate; the specific support, the pH, temperature, specific base selected, and contacting time. In the impregnation method, the support is wetted with a solution, suspension, or colloid containing a compound of oxidized gold, to the point of incipient wetness or to a point of lesser or greater wetness, as desired. Here too, the impregnation conditions can vary, for example, with the specific gold compound, its concentration in the solution or suspension, the particular support, and the impregnation temperature. The support may be treated with multiple impregnations, if desired.

The temperature of the deposition-precipitation and impregnation techniques (or the ion-exchange technique, if that is used) usually ranges from about ambient, taken as 21° C., to about 100° C., but other temperatures may be found to be suitable. Any gold compound can be used to prepare the gold solution or suspension for the deposition-precipitation and impregnation methods, or the ion-exchange method if that is used. Non-limiting examples of suitable gold compounds include chloroauric acid, sodium chloroaurate, potassium chloroaurate, gold cyanide, potassium gold cyanide, gold acetate, diethylamine auric acid trichloride, alkyl gold halides, preferably, alkyl gold chlorides, and alkali aurates, such as lithium aurate, sodium aurate, potassium aurate, rubidium aurate, and cesium aurate. Organo-gold compounds can also be employed. Suitable solvents include, but are not limited to, water and organic solvents, the latter including alcohols (for example, methanol, ethanol, and isopropanol), esters, ketones, and aliphatic and aromatic hydrocarbons. Mixtures of water and organic solvents are also suitably employed. Typically, where a solution is used, the molarity of the soluble gold compound ranges from about 0.0001 M to the saturation point of the soluble gold compound, preferably, from about 0.0005 M to about 0.5 M. If an aqueous solution is used containing oxidized gold salts, the pH of the solution may be adjusted to any value between 5 and 14, preferably, with a base selected, for example, from carbonates, borates, carboxylates, hydroxides, silicates, and mixtures thereof. Optionally, the solution may contain cationic and/or anionic additives which favor stabilization of oxidized gold species, including, for example, certain promoter metal ions (for example, $Li^+$, $Mg^{+2}$, and $La^{+2}$), as well as halides, sulphates, phosphates, carbonates, borates, and carboxylates, such as, acetates, lactates, citrates, maleates, cinnamates, and mixtures thereof.

For illustrative purposes, a deposition-precipitation synthesis is set forth which is suitable for preparing a preferred catalyst composition comprising oxidized gold on a titanium-containing support containing a plurality of titanium species. This description is intended for illustration only and should not be construed to limit the synthetic methods which can be used in preparing the catalyst of this invention. The titanium-containing support is contacted with an aqueous solution of a soluble gold compound, for example, chloroauric acid. The pH is typically adjusted to between about 5 and 14 with any suitable base, such as, sodium hydroxide, sodium carbonate, sodium silicate, sodium acetate, potassium carbonate, cesium hydroxide, lithium carbonate, cesium carbonate, rubidium carbonate, or a mixture thereof. The pH is selected to facilitate, and preferably optimize, the reaction of gold ions with the support. A pH greater than about 7 and less than about 14 is preferred. The mixture is stirred under air at a temperature between about 20° C. and about 80° C. for a time ranging from about 1 hour to about 24 hours. At the end of this period, the solids are recovered, washed with water, the water optionally containing one or more promoter metal salts. Thereafter, the solid is dried under air at a temperature between about 20° C. and about 120° C.

As another illustration, an impregnation synthesis is set forth which is suitable for preparing a preferred catalyst composition comprising oxidized gold on a titanium-containing support having a plurality of titanium species. Again, this description should not be construed to limit the method described herein. In this method, the titanium-containing support may be impregnated with an aqueous solution of a soluble gold compound, for example, chloroauric acid. The pH is typically adjusted to between about 5 and 14 with any suitable base, as mentioned hereinbefore with regard to deposition-precipitation. A pH greater than about 7 and less than about 14 is preferred. Alternatively, the impregnation solution may be prepared with an organic solvent, for example, alcohol, or a mixture of water with an organic solvent. The gold compound and/or other salts employed need not be fully dissolved in the solvent; suspensions can be used. Thereafter, the solid is dried under air at a temperature between about 20° C. and about 120° C. to remove the solvent.

The as-synthesized catalyst may be used without further treatment. Optionally, the as-synthesized catalyst may be calcined under air, or heated in an inert atmosphere, such as nitrogen. The calcination/heating temperature depends upon the particular sample, but may be varied from about 100° C. to about 800° C., preferably, from about 120° C. to about 750° C. Preferably, the temperature is chosen to minimize the reduction of oxidized gold to metallic gold. As an alternative, the as-synthesized catalyst may be conditioned prior to use. The conditioning comprises heating the catalyst, for example, in the oxidation reactor under an atmosphere comprising an inert gas, such as helium, and optionally, one or more compounds selected from hydrocarbons (for example, the olefin to be oxidized), hydrogen, and oxygen at a temperature between about ambient, taken as 21° C., and about 600° C.

Optionally, the catalyst of this invention can contain a promoter metal or a combination of promoter metals. Any metal or metal ion, or combination thereof, which enhances the performance of the catalyst in the oxidation process of this invention can be employed as a promoter metal. Factors contributing to increased performance include, but are not limited to, increased conversion of the olefin, increased selectivity to the olefin oxide, decreased productivity to water, and increased catalyst lifetime. Typically, the valence of the promoter metal ion(s) ranges from +1 to +7; but metallic species may also be present. Non-limiting examples of suitable promoter metals include the metals of Groups 1 through 12 of the Periodic Table of the Elements, as well as the rare earth lanthanides and actinides, as referenced in the *CRC Handbook of Chemistry and Physics*, 75$^{th}$ ed., CRC Press, 1994. Preferably, the promoter metal is selected from silver, Group 1 metals including lithium, sodium, potassium, rubidium, and cesium; Group 2 metals, including beryllium, magnesium, calcium, strontium, and barium; the lanthanide rare earth metals, including cerium, praseodymium, neodymium, promethium, samarium, europium, gadolinium, terbium, dysprosium, holmium, erbium, thulium, ytterbium, and lutetium; and the actinide metals, specifically, thorium and uranium. More preferably, the promoter metal is selected from silver, magnesium, calcium, barium, erbium, lutetium, lithium, sodium, potassium, rubidium, cesium, and combinations thereof. Preferably, the promoter metal excludes palladium, and more preferably, the promoter metal excludes a Group VIII metal, specifically, iron, cobalt, nickel, ruthenium, rhodium, palladium, osmium, iridium, and platinum. As used herein, the word "excludes" means that the total concentration of the Group VIII metal is less than about 0.01 weight percent, preferably, less than about 0.005 weight percent, based on the total catalyst composition.

If one or more promoter metals are used, then the total quantity promoter metal(s) generally is greater than about 0.001 and, preferably, greater than about 0.01 weight percent, based on the total weight of the catalyst. The total quantity of promoter metal(s) is generally less than about 20 and, preferably, less than about 15 weight percent, based on the total weight of the catalyst.

If necessary, the promoter metal(s) can be deposited onto the titanium-containing support simultaneously with the titanium, or alternatively, in a separate step either before or after the titanium. If necessary, the promoter metal(s) can be deposited onto the titanium-containing support simultaneously with the gold, or alternatively, in a separate step either before or after gold is deposited. For the purposes of this discussion, the word "deposit" will include all of the methods of deposition-precipitation, ion-exchange, and impregnation. Alternatively, the promoter metal can be deposited onto a precursor form of the catalyst before the titanium is added, or after it is added, or simultaneously with the titanium. Typically, the promoter metal is deposited from an aqueous or organic solution or suspension containing a promoter metal salt and, optionally, other additives that favor the stabilization of oxidized gold species, as noted hereinbefore. Any salt of the promoter metal can be used; for example, the metal halides, such as the fluorides, chlorides, and bromides; nitrates, borates, silicates, sulfates, phosphates, carbonates, and carboxylates, particularly the acetates, oxylates, cinnamates, lactates, maleates, citrates. Mixtures of the aforementioned salts can be used. If an organic solvent is employed, it can be any of a variety of known organic solvents, including, for example, alcohols, esters, ketones, and aliphatic and aromatic hydrocarbons. Ordinarily, the support is contacted with the solution of the promoter metal salt under conditions which are similar to those used for contacting the support with the gold solution. After the promoter metal is deposited, washing is optional; and if done, the wash liquid preferably contains salts of the desired promoter metals. Afterwards, calcination under air, or heating in an inert gas, or conditioning in the oxidation reactor may optionally be conducted in a manner similar to that described hereinabove for the gold deposition; however, the process conditions of any post-synthesis treatment are preferably chosen to minimize the reduction of oxidized gold to metallic gold.

The process of this invention can be conducted in a reactor of any conventional design suitable for gas or liquid phase processes. These designs broadly include batch, fixed-bed, transport bed, fluidized bed, moving bed, trickle bed, and shell and tube reactors, as well as continuous and intermittent flow and swing reactor designs. The olefin, hydrogen, and oxygen can be contacted together. Alternatively, the process can be conducted step-wise wherein the catalyst is first contacted with oxygen and thereafter the oxygenated catalyst is contacted with a mixture of propylene and hydrogen. Preferably, the process is conducted in the gas phase, and the reactor is designed with heat transfer features for the removal of the heat produced. Preferred reactors designed for these purposes include fixed-bed, shell and tube, fluidized bed, and moving bed reactors, as well as swing reactors constructed from a plurality of catalyst beds connected in parallel and used in an alternating fashion.

The process conditions for the oxidation described herein can vary considerably over a nonflammable and flammable regime. It is beneficial, however, to recognize the conditions which distinguish between nonflammable and flammable mixtures of the olefin, hydrogen, and oxygen. Accordingly, a composition diagram can be constructed or consulted which for any given process temperature and pressure shows the flammable and non-flammable range of reactant compositions, including the diluent, if used. The more preferred reactant mixtures specified hereinabove are believed to lie outside the flammable regime when the process is operated at the more preferred temperatures and pressures specified hereinbelow. Nevertheless, operation within the flammable regime is possible, as designed by one skilled in the art.

Usually, the process is conducted at a temperature which is greater than about ambient, taken as 21° C., preferably, greater than about 70° C., more preferably greater than about 130° C. Usually, the process is conducted at a temperature less than about 300° C., preferably less than about 260° C. Usually, the pressure ranges from about atmospheric to about 400 psig (2,758 kPa), preferably, from about 100 psig (690 kPa) to about 300 psig (2,069 kPa).

In flow reactors, the residence time of the reactants and the molar ratio of reactants to catalyst will be determined by the space velocity. For a gas phase process the gas hourly space velocity (GHSV) of the olefin can vary over a wide range, but typically is greater than about 10 ml olefin per ml catalyst per hour ($h^{-1}$), preferably greater than about 100 $h^{-1}$, and more preferably, greater than about 1,000 $h^{-1}$. Typically, the GHSV of the olefin is less than about 50,000 $h^{-1}$, preferably, less than about 35,000 $h^{-1}$, and more preferably, less than about 20,000 $h^{-1}$. Also, for a gas phase process the total gas hourly space velocity (GHSV) of the feedstream can vary over a wide range, but typically is greater than about 10 ml gas per ml catalyst per hour ($h^{-1}$), preferably, greater than about 100 $h^{-1}$, and more preferably, greater than about 1,000 $h^{-1}$. Typically, the GHSV of the feedstream is less than about 50,000 $h^{-1}$, preferably, less than about 35,000 $h^{-1}$, and more preferably, less than about 20,000 $h^{-1}$. Likewise, for a liquid phase process the weight hourly space velocity (WHSV) of the olefin component can vary over a wide range, but typically is greater than about 0.01 g olefin per g catalyst per hour ($h^{-1}$), preferably, greater than about 0.05 $h^{-1}$, and more preferably, greater than about 0.1 $h^{-1}$. Typically, the WHSV of the olefin is less than about 100 $h^{-1}$, preferably, less than about 50 $h^{-1}$ and more preferably, less than about 20 h$^{-1}$. The gas and weight hourly space velocities of the oxygen, hydrogen, and diluent components can be determined from the space velocity of the olefin taking into account the relative molar ratios desired.

When an olefin having at least three carbon atoms is contacted with oxygen in the presence of hydrogen and the catalyst described hereinabove, the corresponding olefin oxide (epoxide) is produced in good productivity. A preferred olefin oxide is propylene oxide.

The conversion of olefin in the process of this invention can vary depending upon the specific process conditions employed, including the specific olefin, temperature, pressure, mole ratios, and form of the catalyst. For the purposes of this invention, the term "conversion" is defined as the mole percentage of olefin which reacts to form products. Typically, an olefin conversion of greater than about 0.25 mole percent is achieved. Preferably, the olefin conversion is greater than about 1.0 mole percent, more preferably, greater than about 1.5 mole percent, and most preferably, greater than about 2.0 mole percent.

The selectivity to olefin oxide can vary depending upon the specific process conditions employed. For the purposes of this invention, the term "selectivity" is defined as the mole percentage of reacted olefin which forms a particular product, desirably the olefin oxide. The process of this invention produces olefin oxides in unexpectedly high selectivity. Typically the selectivity to olefin oxide is greater than about 70, preferably, greater than about 80, and more preferably, greater than about 90 mole percent.

The productivity of the catalyst, measured as grams of propylene oxide per kilogram catalyst per hour (g PO/kg cat-h) depends upon the specific catalyst used and process conditions, such as, temperature, pressure, and feedrate. The productivity is typically greater than about 30 g PO/kg cat-h, preferably, greater than about 50 g PO/kg cat-h, and more preferably, greater than about 100 g PO/kg cat-h.

The hydrogen efficiency in the process of this invention is advantageously high. More specifically, the water:olefin oxide molar ratio is typically greater than about 1:1, but less than about 30:1, and preferably, less than about 10:1.

In preferred embodiments, the catalyst of this invention exhibits evidence of an improved, long lifetime. The term "lifetime" as used herein, refers to the time measured from the start of the oxidation process to the point at which the catalyst after regeneration has lost sufficient activity so as to render the catalyst useless, particularly commercially useless. As evidence of its long lifetime, the catalyst remains active for long periods of time with little deactivation. Typically, a run time greater than about 40 hours without catalyst deactivation has been achieved in a fixed bed reactor. Preferably, a run time greater than about 100 hours without catalyst deactivation can be achieved. In more preferred embodiments, the catalyst of this invention has been run for more than about 400 hours with little deactivation. The preferred run time between regenerations will depend upon the reactor design and may range from minutes for transport bed reactors to several months for fixed bed reactors.

When its activity has decreased to an unacceptably low level, in preferred embodiments, the catalyst of this invention can be easily regenerated. Any catalyst regeneration method generally known to those skilled in the art can be used with the catalyst of this invention, provided that the catalyst is reactivated for the oxidation process described herein. One suitable regeneration method comprises heating the deactivated catalyst at a temperature between about 150° C. and about 500° C. under an atmosphere of a regeneration gas containing oxygen, hydrogen, water, or mixtures thereof, and optionally an inert gas. A preferred regeneration temperature lies between about 200° C. and about 400° C. The amounts of oxygen, hydrogen, and/or water in the regeneration gas can be any which effectively regenerate the catalyst. Preferably, the oxygen, hydrogen, or water comprises from about 2 to about 100 mole percent of the regeneration gas. Suitable inert gases are non-reactive and include, for example, nitrogen, helium, and argon. The time during which the catalyst is regenerated can range from as short as about 2 minutes to as long as several hours, for example, about 20 hours at the lower regeneration temperatures.

The invention will be further clarified by a consideration of the following examples, which are intended to be purely exemplary of the use of the invention. Other embodiments of the invention will be apparent to those skilled in the art from a consideration of this specification or practice of the invention as disclosed herein. Unless otherwise noted, all percentages are given on a mole percent basis.

The X-ray photoelectron spectra reported in the examples were typically acquired on a Kratos Axis 165 or a PHI 5400 XPS instrument. Typically, the operating parameters for the Kratos Axis instrument were the following: X-ray source, Monochromatic Al Kα (210 watts, 14 kV, 15 m A; Analyzer Pass Energy, 80 eV (survey spectra), 20 or 40 eV (high resolution spectra); Take-Off Angle, 90°; Lens Mode, hybrid; Aperture, slot (3×10 mm) for samples on carbon tape and 2 mm diameter for samples on Al holder; Iris, 50; Analysis Area (16–84 percent signal level), 600 (x)×220µ (y), uncalibrated, 1.5 mm diameter; and Flood Gun conditions: filament current, 2.0 A; charge balance, 3.25 V; bias, 1.0 V. Operating parameters for the PHI 5400 instrument were the following: X-ray source, magnesium Kα (225 watts, 15 kV, 15 mA; Analyzer Pass Energy, 89 eV (survey spectra), 17.8 eV (high resolution spectra); Take-Off Angle, 45°; Lens Mode, 3:1 magnification; Aperture, slot (10×3 mm) (3×1 mm analysis area); Iris, 50; Flood Gun not used. Samples were prepared by either smearing the powdered sample onto a double-sided conductive carbon tape or by pressing the powdered sample into blind holes (3 mm dia.) in an aluminum sample holder. Spectra were recorded in the Si(2p) and Au(4f) spectral regions. The Si(2p) spectra were used to calibrate the binding energy scale to account for surface electrical charging which occurred during analysis. Bulk gold exhibited 4f lines at 84.0 and 87.7 eV with a theoretical intensity ratio of the 7:2 and 5:2 spin orbit doublet of 4:3.

EXAMPLE 1

Nanometer size crystals of a titanosilicate were prepared using tetraethylorthosilicate (TEOS), titanium n-butoxide, and tetrapropylammonium hydroxide (TPAOH), in an aqueous reaction mixture having the following molar composition: 1.0 SiO$_2$: 0.015 TiO$_2$: 35HO: 0.33 TPA. A solution containing TEOS and isopropyl alcohol in a ratio of 5:1 was added with vigorous stirring to a solution of TPAOH (20 weight percent). After 20 min of agitation a solution of titanium tetra(n-butoxide) in dry isopropyl alcohol (1:5 ratio) was added to the first solution slowly with vigorous stirring. The clear solution was stirred for 1 hour followed by a slow addition of cooled deionized water. The synthesis mixture was sealed in an autoclave with stirring at 1 70° C. under autogeneous pressure for 4 days. A crystalline solid was recovered by centrifugation at 2,000 RPM for 3 hours. The crystalline solid was washed twice with hydrochloric acid (0.1 M), washed with deionized water, and dried at 70°

C. for 2 hours. The solid was thereafter calcined at 550° C. in air for 8 hours. The product, a titanosilicate, comprised orthorhombic crystals of an average size of 100 nm, as measured by TEM, with an MFI structure type, as determined by powder XRD. No bulk titanium dioxide was found. Si:Ti atomic ratio was 90:1. Ti-XPS showed two titanium peaks, at 460 eV and 458 eV, interpreted as 81 percent low coordination (framework) and 19 percent high coordination grafted) titanium, respectively.

Using overhead stirring chloroauric acid ($HAuCl_4 \cdot 3H_2O$, 0.171 g) was added to deionized water (171 ml). The resulting yellow solution was heated in a water bath to 71° C. (pH 2.4). The pH was adjusted to 8.5 with sodium carbonate (0.5 N) and then stirred for 80 min at 71° C. The solution became colorless, and the pH measured 8.97. Magnesium nitrate (0.236 g) was added to the solution with stirring, 5 min after which the pH was 8.6. The stirring was stopped, and the beaker containing the solution was placed in a cold water bath for 20 min. At 24° C, the pH of the solution measured 9.12. The titanosilicate (5 g) prepared herein was added to the gold solution with vigorous overhead stirring. The suspension was stirred for 2 hours; the pH measured 8.29. The solids were filtered and washed with deionized water (185 ml). Then, the solids were calcined as follows: heated in flowing air from room temperature to 110° C. in 30 min and held at 110° C. for 12 hours, heated from 110° C. to 700° C. in 5 hours and kept at 700° C. for hours to yield the catalyst of the invention.

The catalyst, having a faint pink color around the edges of the particles, was essentially free of metallic gold, as determined by HR-TEM. A small peak was observed by Mie scattering. Gold was present essentially as oxidized gold, as determined by XPS in combination with HR-TEM. Elemental analysis, by weight was as follows: 0.024 percent Au, 51 percent Si, 0.79 percent Ti, 0.23 percent Na, 0.016 percent K, 0.12 percent Mg, as determined by neutron activation analysis (NAA).

The catalyst was tested in the hydro-oxidation of propylene to propylene oxide as follows. The catalyst (2 g) was loaded into a fixed-bed, continuous flow reactor [0.5 inch (12.5 mm) diameter×12 inches (30 cm) length)] and activated as follows. At 140° C., the catalyst was heated under helium for 5 hours, then heated under a flow of propylene and hydrogen for 10 min, then oxygen was added. Feedstream composition was 10 percent hydrogen, 10 percent oxygen, and 20 percent propylene, the balance being helium. Propylene, oxygen and helium were used as pure streams; hydrogen was mixed with helium in a 20 $H_2$/80 He (v/v) mixture. After a constant rate of propylene oxide, production was obtained for 1 hour, the temperature was ramped in 15° C. intervals up to the operating temperature. Operating pressure was atmospheric. Products were analyzed using either on-line gas chromatography (Chrompack™ Poraplot™ S column, 25 m) or mass spectrometry.

At 186° C. and a residence time of 1.74 sec (GHSV 2069 $h^{-1}$) and after 68 hours on stream, the catalyst exhibited a propylene conversion of 1.5 percent, a propylene oxide (PO) selectivity of 90 percent, a productivity of 35 g PO/kg cat-h, and a water:PO molar ratio of 3.3:1.

EXAMPLE 2

Nanometer size crystals of titanosilicate were prepared using tetraethylorthosilicate, titanium n-butoxide, and tetrapropylammonium hydroxide (TPAOH) template in an aqueous reaction mixture having the following molar composition: 1.0 $SiO_2$: 0.025 $TiO_2$: 36 $H_2O$: 0.235 TPAOH. The reaction mixture was prepared by first mixing the tetraethylorthosilicate and titanium n-butoxide in a stainless steel container under an inert gas atmosphere, followed by heating at 80° C. for 3 h. The resulting mixture and a solution of TPAOH (40 weight percent) were both cooled in an ice bath to 5° C. The TPAOH solution was slowly added with vigorous stirring to the mixture of alkoxides to yield a gel. Chilled, deionized water was added to the gel, and the gel was warmed to room temperature. The gel was aged for 10 hours and then loaded into a stainless steel autoclave which was heated at 160° C. and 300 psig (2068 kPa) for 6 days. At the end of this period, the autoclave was cooled, and the contents were centrifuged at 2,000 rpm for 3 hours to yield a translucent white solid. The solid was discarded, and the liquor from the centrifugation was heated to 80° C. for 5 hours to rid the liquor of ethanol and residual amine. The liquor was cooled to room temperature and its pH was adjusted from 12 to 7 with nitric acid (2M). A suspension formed. The suspension was centrifuged at 2,000 rpm for 30 min to yield a white quasi-crystalline solid. The solid was dried at 80° C. for 12 h, then calcined at 550° C. in air for 8 hours to yield the titanosilicate support. The product was in the form of irregular shaped, thick plates having an average size of 80 nm, as viewed by HR-TEM. A powder XRD pattern showed an orthorhombic structure of MFI type. No bulk titanium dioxide was found by XRD. Si:Ti atomic ratio was 46:1. Ti-XPS showed two titanium peaks at 460 eV and 458 eV, interpreted as 61 percent low coordinate (framework) and 39 percent high coordinate (grafted) titanium, respectively.

Using overhead stirring, chloroauric acid (0.171 g) was added to deionized water (171 ml). The transparent yellow solution was heated in a water bath to 70° C., having a pH of 2.4. The pH was adjusted to 8.6 with a solution of sodium carbonate (pH 0.5 N). The solution became colorless. The solution was stirred for 75 min at 70° C. The pH measured 9.03. Upon addition of magnesium nitrate (0.236 g) the pH changed to 8.64 after 5 min. Stirring was stopped, and the beaker containing the solution was placed in a cold water bath for 25 min. At 21° C. the pH of the solution measured 9.11. With overhead stirring, the titanosilicate (5 g) prepared herein was added to the solution, and the resulting mixture was stirred for 2 hours. Sodium carbonate (0.5 N) was added whenever necessary to maintain the pH at 8. After 2 hours the pH measured 8.54 at 21° C. The solids were filtered and washed with deionized water (185 ml). The solids were calcined according to the following procedure: heated in flowing air from room temperature to 110° C. in 30 min and kept at 110° C. for 12 hours, then heated from 110° C. to 700° C. in hours and kept at 700° C. for 10 hours to yield a catalyst of the invention.

The catalyst, having a white color, was essentially free of metallic gold, as determined by HR-TEM. No Mie scattering was observed. Gold was present essentially as oxidized gold, as determined by XPS. Elemental analysis, by weight: 0.015 percent Au, 47 percent Si, 1.35 percent Ti, 0.46 percent Na, and 0.14 percent Mg, as determined by NAA.

The catalyst (2 g) was evaluated in the hydro-oxidation of propylene to propylene oxide in the manner described in Example 1. At 192° C. and a residence time of 1.71 sec (GHSV 2105 $h^{-1}$) and after 450 hours on stream, the catalyst exhibited a propylene conversion of 1.5 percent, a PO selectivity of 92 percent, a productivity of 37 g PO/kg cat-h, a water:PO molar ratio of 4.0:1, and 0.33 weight percent PO in the reactor outlet.

EXAMPLE 3

Using overhead stirring chloroauric acid (0.171 g) was added to deionized water (171 ml). The transparent yellow solution was heated in a water bath to 71° C., pH of 2.36. The pH was adjusted to 8.63 with sodium carbonate (0.5 N). The solution became colorless. The solution was stirred for 80 min at 71° C. The pH measured 8.85. Upon addition of magnesium nitrate (0.237 g) the pH changed to 8.64 after 5 min at 71.7° C. Stirring was stopped and the beaker with the solution was placed into a cold water bath for 20 min. At 21° C. the pH of the solution measured 9.13. With overhead stirring the titanosilicate (5 g) of Example 1 was added, and stirring was continued for 2 hours. The pH became 8.37 at 20° C. The solids were filtered and washed with deionized water (185 ml). The solids were calcined in the manner set forth in Example 2 to yield a catalyst of this invention. The catalyst had only a faint color, which indicated that the gold was essentially oxidized. The catalyst (2 g) was evaluated in the hydro-oxidation of propylene to propylene oxide as in Example 1. At 163° C. and a residence time of 1.83 sec (GHSV 1967 $h^{-1}$), and after 21 hours on stream, the catalyst exhibited a propylene conversion of 2.0 percent, a PO selectivity of 89 percent, a productivity of 49 g PO/kg cat-h, a water:PO molar ratio of 3.15:1, and 0.44 percent PO in the reactor outlet with very little deactivation. At the peak activity (6 hours on stream) this catalyst showed 2.6 percent conversion, 88.5 percent selectivity, a productivity of 61 g PO/kg cat-h, a water:PO molar ratio of 3.7:1, and 0.54 weight percent PO in the outlet from the reactor.

EXAMPLE 4

Using overhead stirring chloroauric acid (0.171 g) was added to deionized water (171 ml). The transparent yellow solution was heated in a water bath to 70° C., pH of 2.37. The pH was adjusted to 8.67 with an aqueous solution of rubidium carbonate (1 N). The solution became colorless. The solution was stirred for 2 hours at 69° C. The pH became 9.1. Upon addition of magnesium nitrate (0.116 g) the pH changed to 8.94 after 5 min at 66.1° C. Stirring was stopped, and the beaker with the solution was placed into a cold water bath for 20 min. At 17.9° C. the pH was adjusted to 9.54 with the rubidium carbonate solution. With overhead stirring the titanosilicate (5 g) of Example 2 was added. The mixture was stirred for 2 hours. The pH value measured 8.2 at 21.8° C. The solids were filtered and washed with deionized water (100 ml). The solids were calcined as described in Example 2 to yield a catalyst of the invention. Elemental analysis, by weight, was as follows: 0.050 percent Au, 46 percent Si, 1.22 percent Ti, 1.6 percent Rb, 0.010 percent K, 0.0028 percent Na, by NAA. The catalyst had only a faint color, which indicated that the gold was essentially oxidized.

The catalyst (2 g) was evaluated in the hydro-oxidation of propylene to propylene oxide. At 180° C. and a residence time of 1.76 sec (GHSV 2045 $h^{-1}$) and after 120 hours on stream, the catalyst exhibited a propylene conversion of 2.5 percent at a PO selectivity of 91 percent, a productivity of 60 g PO/kg cat-h, a water:PO molar ratio of 4.0.1, and 0.53 weight percent PO in the reactor outlet with very little deactivation.

The same catalyst (3 g) was evaluated in the hydro-oxidation of propylene to propylene oxide in a pressure reactor under 230 psia (1,586 kPa) with a feed of 20 percent propylene, 7.5 percent oxygen, and 7.5 percent hydrogen in helium. At 190° C. and a residence time of 2.33 sec and after 15 hours on stream, the material showed 1.8 percent propylene conversion at 92 percent PO selectivity and a productivity of 270 g PO/kg cat-h.

EXAMPLE 5

Using overhead stirring chloroauric acid (0.088 9) was added to deionized water (85.5 ml). The transparent yellow solution was heated in a water bath to 72° C. (pH 2.18). The pH was adjusted to 8.59 with an aqueous solution of rubidium carbonate (1 N). The solution became colorless. The mixture was stirred for 80 min at 69.5° C. The pH became 9.13. Stirring was stopped and the beaker with the solution was placed in a cold water bath. At 23.3° C. the pH of the solution became 9.43. With overhead stirring the titanosilicate (2.5 g) of Example 1 was added, and the resulting mixture was stirred for 2 hours. The pH kept dropping, so additional rubidium carbonate solution was added to keep the pH at about 8. The final pH value was 8.31 at 21° C. The solids were filtered and washed with deionized water (90 ml). The solids were calcined according to the procedure of Example 2 to yield a catalyst of this invention. Oxidized gold comprised 46 weight percent of the total gold content, as determined by XPS.

The catalyst (2 g) was evaluated in the hydro-oxidation of propylene to propylene oxide, as described in Example 1. At 180° C. and a residence time of 1.76 sec (GHSV 2045 $h^{-1}$) and after 120 hours on stream the material achieved 2.2 percent propylene conversion at 90 percent PO selectivity, a productivity of 53 g PO/kg cat-h, a water:PO molar ratio of 6.6:1, and 0.46 weight percent PO in the reactor outlet.

EXAMPLE 6

Using overhead stirring a solution (17.1 ml) comprising chloroauric acid (0.171 g) and deionized water (171 ml) was further diluted with deionized water (153.9 ml). The transparent light-yellow solution was heated in a water bath to 72.7° C. (pH 2.79). The pH was adjusted to 8.68 with an aqueous solution of rubidium carbonate (1 N). The solution became colorless. The solution was stirred for 80 min at 75.7° C. The pH changed to 8.78. Upon addition of magnesium nitrate (0.141 g) the pH changed to 8.47 after 5 min at 76° C. Stirring was stopped, and the beaker containing the solution was placed in a cold water bath for 20 min. At 24.3° C. the pH value was 9.18. With overhead stirring the titanosilicate (3 g) of Example 1 was added, and the mixture was stirred for 2 hours. The pH value kept dropping, so more rubidium carbonate solution was added to keep the pH at about 8. After 2 hours the pH value measured 8.03 at 20.7° C. The solids were filtered and washed with deionized water (90 ml). The solids were calcined according to the procedure of Example 2 to yield a catalyst of this invention. Elemental analysis, by weight, was as follows: 0.011 percent Au, 47 percent Si, 1.12 percent Ti, 0.93 percent Rb, 0.090 percent Mg, 0.0052 percent Na, by NAA. The catalyst had only a faint color, which indicated that the gold was essentially oxidized.

The catalyst (2 g) was evaluated in the hydro-oxidation of propylene to propylene oxide in the manner described in Example 1. At 200° C. and residence time of 1.69 sec (GHSV 2130 $h^{-1}$), and after 120 hours on stream the catalyst exhibited a propylene conversion of 1.8 percent, a PO selectivity of 89 percent, a productivity of 42 g PO/kg cat-h, a water:PO molar ratio of 3.8:1, and 0.39 weight percent PO in the reactor outlet.

EXAMPLE 7

A 14 L stainless steel container with a cover was purged for 15 minutes with dry nitrogen. Tetra(ethyl)orthosilicate (11,276 g) was transferred into the container. Titanium butoxide (236.4 g) was added to the silicate with vigorous stirring. The resulting solution was heated to 91° C. with continuous agitation under the nitrogen purge, and kept at this temperature for a total heating time of 2 hours. The solution was then cooled to 1.9° C. in an ice bath for 2 hours. An aqueous solution of tetrapropylammonium hydroxide (9874 g, 40 weight percent TPAOH) having a low alkali content (less than 20 ppm Na) was placed into a 16 gallon polypropylene container. Deionized water (5814 g) was added to the TPAOH solution with stirring. The container was placed into an ice bath. The TPAOH solution was also pumped through an external SS ¼ inch (0.6 cm) coil immersed in a dry ice—acetone bath (t is approximately −25° C.) to achieve faster cooling and better temperature control. The solution was cooled down to −4° C. The cold alkoxide solution was pumped into the 16 gallon container at the rate of 150 ml/min. The temperature of the mixture slowly rose reaching −2° C. after the addition of about ½ of the alkoxide solution. Finally, deionized water (5432 g) was added to the mixture with agitation. The temperature of the final mixture was 8.2° C. The mixture was stirred for 18 hours at room temperature.

Thereafter, the hydrothermal synthesis was conducted in a Stainless Steel autoclave with 200 rpm stirring. The autoclave was heated to 160° C. and kept at this temperature for 4 days. The reactor was then cooled to room temperature, and the product was pumped out from the reactor. The product contained a large organic layer that was separated from the rest of the mixture. The pH of the aqueous milky liquid was adjusted to about 8.7 with nitric acid (1.5N), and the product was recovered by centrifugation at 3000 rpm. The solid was re-dispersed in deionized water and centrifuged again. The resulting solid was dried at 110° C. for 12 hours, followed by calcination in an air-blown oven. The material was heated to 550° C. in 5 hours, followed 5 hours heating at 550° C. A powder XRD analysis showed that the material was a pure phase of the MFI type. Ti-XPS showed 87 percent low coordinate and 13 percent high coordinate titanium.

An aqueous solution of cesium hydroxide (0.296 g, 50 percent weight) was added to deionized water (19.85 g). The pH of the resulting solution was 12.6. Sodium acetate trihydrate (0.128 g) was dissolved in the CsOH with stirring. The pH of the solution changed to 12.5. Hydrogen tetrachloroaurate trihydrate (0.008 g) was added to the solution and dissolved with stirring. The pH of the solution remained unchanged. The titanosilicate support (5 g, 2 mm particles), prepared hereinabove, was placed into a 250 ml round bottom flask. The flask was connected to a rotary evaporator and pumped to 30 mm Hg. The titanosilicate was heated under vacuum at 80° C. for 1 hour, then cooled to room temperature. The titanosilicate was slowly impregnated with the gold solution (7.63 g) under vacuum and kept at room temperature for 2 hours. Finally, the impregnated material was heated at 80° C. undervacuum for 2.3 hours. The catalyst had only a faint color, which indicated that the gold was essentially oxidized.

The catalyst (2 g) was loaded into a 0.5 inch (12.5 mm) ID SS fixed bed continuous flow reactor. The catalyst was heated at 140° C. under a flow of helium for 4 hours, then under a flow of propylene and hydrogen for about 10 min, and finally oxygen was added to the feed. Propylene, oxygen and helium were used as pure streams; hydrogen was mixed with helium in a 20:80 by volume mixture. Feedstream composition was 10 percent hydrogen, 10 percent oxygen and 20 percent propylene, the balance being helium. Operating pressure was kept at 10 psig (69 kPa). Products were analyzed using on-line gas chromatography (Chromopack Poraplot S column, 25 m) and/or mass spectrometry. At 190° C. and a residence time of 1.72 sec, after 58 hours on stream the catalyst exhibited a propylene conversion of 3.5 percent, a selectivity to propylene oxide of 92.6 percent, a propylene oxide productivity of 80 g/kg cat h and water:PO molar ratio of 4.5:1. The same performance was observed after 82 hours of operation.

EXAMPLE 8

Potassium hydroxide (0.27 g) was added to deionized water (79.45 g) with stirring. Sodium acetate trihydrate (1.43 g) was dissolved in the above solution with stirring. Hydrogen tetrachloroaurate trihydrate (0.08 g) was added to the solution and dissolved with stirring to form after 30 min a clear solution having a pH of 12.3. A support (40 g), comprising the titanosilicate of Example 7 bound with 18 weight percent silica into ⅛ inch (0.32 cm) extrudates, was placed into a 500 ml round bottom flask. The flask was connected to a rotary evaporator and pumped to 30 mm Hg. The titanosilicate was heated under vacuum at 80° C. for 1.5 hours. The flask was cooled to room temperature and kept at room temperature for 30 min. The titanosilicate was slowly impregnated with the gold solution (38.24 g) under vacuum and kept at room temperature for 2 hours. The impregnated material was heated at 80° C. under vacuum for 2.25 hours to yield the catalyst of this invention. The catalyst had only a faint color, indicating that the gold contained therein was essentially oxidized.

The catalyst (20 g) was evaluated in the hydro-oxidation of propylene to propylene oxide in the manner described in Example 7, with the exception that the WHSV was 11.3 h$^{-1}$ and the pressure was 215 psig (1482 kPa). Products were analyzed using on-line mass spectrometry. At 160° C. after 20 hours on stream the catalyst exhibited a propylene conversion of 1.45 percent, a selectivity to propylene oxide of 97 percent, and a water:PO molar ratio of 6.2:1. After 70 hours on stream the propylene conversion was 1.25 percent, the selectivity to propylene oxide was 96 percent, and water:PO molar ratio was 8.1:1.

EXAMPLE 9

A crystalline titanium silicate (3 g), obtained as in Example 7, was calcined at 550° C. in air for 4 hours and cooled to room temperature. An ethanol solution containing sodium acetate (0.17 g in 15 g ethanol) was prepared. To this solution was added an ethanol solution containing chloroauric acid (0.015 g in 10 g of ethanol). The resulting solution was used to impregnate the titanium silicate by incipient wetness. The impregnated silicate was air dried to yield a catalyst comprising oxidized gold on a titanium-containing support. The catalyst was a white color, indicative of a catalyst containing oxidized gold. No metallic gold was found by HR-TEM or XPS. No oxidized gold was found by XPS. It is noted that the gold loading was very low, and the XPS signal for oxidized gold is typically weak.

The catalyst (2 g) was evaluated in the hydro-oxidation of propylene to propylene oxide using the following feedstream: propylene (35 percent), hydrogen (10 percent), oxygen (10 percent), balance helium; and in the manner described in Example 1. At 15 psig (103 kPa), a total flow of 200 sccm and a temperature of 200° C., the propylene conversion was 2.3 percent at a selectivity of 88 percent to propylene oxide.

EXAMPLE 10

Crystalline titanium silicate (15 g), prepared as in Example 7, was calcined in air to 600° C. for 8 hours and cooled to room temperature. A methanol solution containing sodium acetate (0.20 g in 25 g methanol) was prepared, and to this solution was added a second methanol solution containing chloroauric acid (0.06 g in 5 g methanol). The resulting solution was used to impregnate the titanium silicate by incipient wetness. The impregnated silicate was thereafter dried in a vacuum oven for 30 min and then heated in the oven at 60° C. for 1 hour to yield a catalyst comprising gold on a titanium-containing support. HR-TEM showed a few gold particles. Mie scattering showed a weak band for metallic gold. As determined by XPS, 40 weight percent of the total gold content was oxidized.

The catalyst (3.0 g) was evaluated in the hydro-oxidation of propylene to propylene oxide in the manner similar to that of Example 1. The feedstream comprised propylene (35 percent), hydrogen (10 percent), oxygen (10 percent), the balance being helium. Process conditions were: 225 psig (1551 kPa) at a total flow of 1,500 standard cubic centimeters per minute (sccm). At a temperature of 170° C. the propylene conversion was 1.5 percent with a selectivity to propylene oxide of 99 percent and a water:PO molar ratio of 3.2:1.

EXAMPLE 11

Tetraethylorthosilicate (50 g) was cooled to under 5° C. in an ice-bath, and while stirring titanium (IV) tetra(ethoxide) (0.51 g) was added. To this cooled mixture, a cold (less than 5° C.) solution of tetrapropylammonium hydroxide (TPAOH, 43.9 g; 40 percent in water) and water (43.5 g) were slowly added dropwise at a rate such that no solid phase became visible. Following addition of the TPAOH solution, the mixture was hydrolyzed at room temperature on a gyrotary shaker for 24 hours. The hydrolyzed suspension was then heated at 95° C. for 64 hours. Following crystallization, the suspension was centrifuged at 16,400 rpm for 2 hours, and a solid phase was recovered by decanting the liquor. The solid phase was redispersed in fresh water, and the suspension was centrifuged as described above. This rinsing process was repeated 3 times. The resulting purified suspension was freeze dried to obtain a powder, which was identified by XRD to be a titanosilicate of MFI structure. Crystal size was on average 46–60 nm. XPS showed peaks at 460 eV and 458 eV, attributed to framework and grafted titanium, respectively.

Using overhead stirring chloroaurc acid (0.069 g) was added to deionized water (68.5 ml). The resulting transparent yellow solution was heated in a water bath to 70° C. (pH 2.30). The pH was adjusted to 8.60 with an aqueous solution of sodium carbonate (0.5 N). The solution became colorless. The mixture was stirred for 80 min at 73.8° C. The pH became 9.10. Magnesium nitrate hexahydrate (0.096 g) was added to the solution. After stirring for 5 min the pH was 8.73 at 72.7° C. Then, stirring was stopped and the beaker with the solution was placed in a cold water bath for about 20 min. At 20.1° C. the pH of the solution became 9.26. With overhead stirring the titanosilicate (2.0 g) was added, and the resulting mixture was stirred for 2 hours. The pH kept dropping, so additional sodium carbonate solution was added to keep the pH at about 8. The final pH value was 8.22 at 21.1° C. The solids were filtered and washed with deionized water (90 ml). The solids were calcined according to the procedure of Example 2 to yield a catalyst of this invention. The catalyst had only a faint color, indicating that the gold contained therein was essentially oxidized.

The catalyst was evaluated in the hydro-oxidation of propylene to propylene oxide in the manner described in Example 1, with the exception that the operating temperature was 180° C., the pressure was 10 psig (69 kPa), and the residence time was 1.76 sec (GHSV, 2,045 h$^{-1}$). Under these operating conditions, the catalyst exhibited a propylene conversion of 2.0 percent, a propylene oxide selectivity of 89.9 percent, a $H_2O$:PO molar ratio of 4.7:1, and a propylene oxide productivity of 54 g/kg cat-h.

EXAMPLE 12

The catalyst of Example 4 was evaluated in the hydro-oxidation of 1-butene to 1-butene oxide. The hydro-oxidation was conducted as in Example 1, with the exception that the feedstream comprised 30 percent 1-butene, 8 percent oxygen, 8 percent hydrogen, and the balance helium. At 170° C., atmospheric pressure, and a total flow of 150 cm$^3$/min, the initial 1-butene conversion was 0.7 percent at a selectivity to 1-butene oxide of 86 percent. At 20 hours on stream, the conversion was 0.3 percent at a selectivity to 1-butene oxide of 85 percent.

EXAMPLE 13

A catalyst (2 g) comprising oxidized gold on a ⅛ inch (0.32 cm) titanium-silicate extrudates containing 8 percent silica binder were evaluated in the hydro-oxidation of butadiene. Gold was deposited by the deposition-precipitation procedure as follows. Using overhead stirring chloroauric acid (9.48 g) was added to deionized water (9.55 kg). The transparent yellow solution was heated to 73° C. (pH 2.39). The pH was adjusted to 8.67 with an aqueous solution of rubidium carbonate (1 N). The solution became colorless. The mixture was stirred for 2 hours at 72.1° C. The pH became 8.96. Magnesium nitrate hexahydrate (6.15 g) was added to the solution. After stirring for 5 min the pH was 8.74 at 71.9° C. Then, stirring was stopped and the solution was cooled for 12 hours with constant agitation. At 22.8° C. the pH of the solution became 9.16. The pH was adjusted to 9.6 with 1 N solution of rubidium carbonate. With overhead stirring the titanosilicate extrudate (280 g) was added, and the resulting mixture was stirred for 8 hours. The final pH value was 7.96 at 27.2° C. The solids were filtered and washed with 500 ml of rubidium carbonate solution at pH=9.4. The solids were calcined in the air blown oven by heating from room temperature to 110° C. in 30 min, followed by 4 hours at this temperature, then heated to 700° C. in 5 hours followed by 5 hours at 700° C. to yield a catalyst of this invention.

The catalyst was evaluated in the hydro-oxidation of butadiene, in a manner similar to that described in Example 1. The feedstream comprised 1,3-butadiene (20 percent), oxygen (10 percent), hydrogen (10 percent); propane as an internal standard (4.2 mole percent), the balance being helium. The formation of 1,3-butadiene mono-oxide was confirmed by gas chromatography. Carbon dioxide was observed to be the major by-product. The catalyst was tested at a 280° C. bed temperature after about hours on stream at lower temperatures followed by 12 hours purge with helium at 140° C. Process conditions and results are summarized in Table 1.

TABLE 1

Hydro-Oxidation of 1,3-Butadiene (BD) to 1,3-Butadiene Mono-oxide (BO)[a,b]

| Time on Stream, min | BD Conversion, mol % | BO Selectivity, mol % |
|---|---|---|
| 35 | 4.2 | 83.5 |
| 55 | 3.4 | 84.4 |
| 75 | 2.9 | 83.4 |

[a]Feedstream (mole percentages): 1,3-butadiene (20 percent), oxygen (10 percent), hydrogen (10 percent), propane (4.2 percent), balance helium; 200° C.; atmospheric pressure; residence time, 3 sec (GHSV 1,200 h$^{-1}$)
[b]GC Response Factors for BD and BO were assumed to be the same. The response factor for $CO_2$ was taken as 1.365 times larger than that of BD.

EXAMPLE 14

A mixture of barium and titanium alkoxides (Gelest, Inc., Tullytown, Pa.; DBATI50, 12.51 g of a 0.5 M solution containing 6.7–7.0 weight percent barium and 2.3–2.5 weight percent titanium) was dissolved in isopropanol (200 ml). Silica (PQ HP321, 30.2 g), which had been calcined at 300° C., was added to the solution, and the resulting mixture was stirred overnight. The solvent was removed at 350° C. under vacuum over 1 hour. The solid residue was dried at 110° C. for 5 hours, calcined from 110° C. to 600° C. in air over hours and held at 600° C. for 4 hours to yield a titanium-containing support.

Chloroauric acid (0.1514 g) was dissolved in water (320 ml). The solution was heated to 70° C., and the pH was adjusted to 8.0 with sodium carbonate. The solution was then cooled to room temperature. The titanium-containing support (6.29 g) was added to the gold solution. The pH of the solution decreased; sodium carbonate was added to maintain the pH at 7.5. The mixture was stirred for 1 hour. The solids were filtered, rinsed with water (100 ml at pH 7.5), and filtered. The rinsed solids were dried at 110° C. for 5 hours, then calcined in air from 110° C. to 425° C. in 5 hours, and then held at 425° C. for 4 hours to yield a catalyst of the invention. Elemental analysis was: 940 ppm Au; 0.97 percent Ti; 1290 ppm Na; 2.40 percent Ba; by weight, as determined by NAA. The catalyst contained some gold particles of 3.5 nm size. Using Energy Dispersive X-ray spectroscopy (EDS) on the HR-TEM, it was found that in-between the 3.5 nm gold particles, the catalyst also contained gold which was less than 1 nm. About 30 weight percent of the gold was oxidized, as measured by XPS.

The catalyst was evaluated in the hydro-oxidation of propylene to propylene oxide in the manner described in Example 1 using on-line mass spectrometry for the analysis. The process was run for about 4 hours at 150° C.; then the catalyst was regenerated at 425° C. under a mixture of oxygen (20 volume percent) and water (1 volume percent), the balance being helium. After the first regeneration, the hydro-oxidation process was run at 150° C. for about 5 hours, and then the catalyst was regenerated a second time at 450° C. under the mixture of oxygen, water, and helium. After the second regeneration, the catalysts was evaluated in the hydro-oxidation process at 150° C, with the results shown in Table 2.

TABLE 2

Hydro-Oxidation of Propylene (PP) to Propylene Oxide (PO)[a]

| Temperature ° C. | Time on Stream (h) | Conv PP (mole %) | PO Sel (mole %) |
|---|---|---|---|
| 140 | 0.4 | 1.6 | 96 |
| 140 | 1.8 | 0.80 | 95 |
| 140 | 2.3 | 0.83 | 95 |
| Regenerate 425 | | | |
| 140 | 0.4 | 2.1 | 97 |
| 140 | 1.5 | 1.3 | 97 |
| 140 | 4.0 | 1.2 | 97 |
| Regenerate 450 | | | |
| 150 | 0.5 | 2.0 | 96 |
| 150 | 1.5 | 1.5 | 96 |
| 150 | 4.0 | 1.4 | 96 |

[a]Feedstream (mole percent): 20 percent propylene, 10 percent oxygen, 10 percent hydrogen, balance helium; 150° C., pressure atmospheric, GHSV 960 h$^{-1}$

EXAMPLE 15

A titanosiloane polymer described as diethoxysiloxane-ethyltitanate copolymer (Gelest, Inc., Tullytown, Pa.; PSITI-019, 22.43 g containing 19.1–19.6 percent silicon and 2.1–2.3 percent titanium) was dissolved in isopropanol (150 ml). Silica (PQ HP 321; 20.3 g which had been calcined at 300° C.) was added to the solution, and the mixture was stirred overnight. The solvent was removed at 35° C. under vacuum on a rotary evaporator. The solid residue was heated to 100° C. under vacuum and held at 100° C. for 1 hour. The material was dried at 110° C. for 5 hours and then calcined from 110° C. to 600° C. in air over 5 hours and held at 600° C. for 4 hours to yield a titanium-containing support.

Chloroauric acid (0.1503 g) was dissolved in water (350 ml). The solution was heated to 70° C.; the pH was adjusted to 8.0 with sodium carbonate; and the solution was cooled to room temperature. The titanium-containing support (6.03 g) was added to the gold solution. The pH of the solution decreased; sodium carbonate was added to maintain the pH at 7.5. The mixture was stirred for 1 hour. The solids were filtered, rinsed with water (100 ml, pH 7.5), and filtered again. The solids were dried at 110° C. for hours, then calcined in air from 110° C. to 425° C. in 5 hours, and then held at 425° C. for 4 hours. The solids were taken out of the oven, then returned to the oven at 300° C. and heated in 1 hour to 425° C., then held at 425° C. for 2 hours to obtain the catalyst of the invention. Elemental analysis was: 610 ppm Au; 1.50 percent Ti; 4700 ppm Na, by weight. The catalyst contained gold particles of 3.5 nm size. Using EDS on the HR-TEM, it was found that in-between the 3.5 nm gold particles, the catalyst also contained gold which was less than 1 nm. Oxidized gold comprised 40 weight percent of the total gold content, as measured by XPS.

The catalyst was evaluated in the hydro-oxidation of propylene to propylene oxide in the manner described in Example 1. The process was run for about 4 hours at 150° C.; then the catalyst was regenerated at 425° C. under a mixture of oxygen (20 volume percent) and water (1 volume percent), the balance being helium. After the first regeneration, the hydro-oxidation process was run at 150° C. for about 5 hours, and then the catalyst was regenerated a second time at 450° C. under the mixture of oxygen, water, and helium. After the second regeneration, the catalyst was evaluated in the hydro-oxidation process at 150° C. with the results shown in Table 3.

TABLE 3

Hydro-Oxidation of Propylene (PP) to Propylene Oxide (PO)[a]

| Temperature | Time on Stream (h) | Conv PP (mole %) | PO Sel (mole %) |
|---|---|---|---|
| 140 | 0.4 | 1.5 | 96 |
| 140 | 1.8 | 0.97 | 96 |
| 140 | 2.3 | 0.95 | 96 |
| Regenerate 425 | | | |
| 140 | 0.4 | 1.7 | 97 |
| 140 | 1.5 | 1.1 | 96 |
| 140 | 4.0 | 0.66 | 96 |
| Regenerate 450 | | | |
| 150 | 0.5 | 1.7 | 96 |
| 150 | 1.5 | 1.2 | 96 |
| 150 | 4.0 | 0.95 | 96 |

[a]Feedstream (mole percent): 20 percent propylene, 10 percent oxygen, 10 percent hydrogen, balance helium; 150° C., pressure atmospheric; GHSV 960 h$^{-1}$

EXAMPLE 16

Chloroauric acid (0.1513 g) and barium nitrate (0.3037 g) were dissolved in water (350 ml). The resulting solution was heated to 70° C.; the pH was adjusted to 7.0 with sodium carbonate; and the solution was cooled to room temperature. A titanium-containing support (6.05 g), identical to that used in Example 15, was added to the gold and barium solution. The pH of the solution decreased; sodium carbonate was added to maintain the pH at 7.0. The mixture was stirred for 1 hour. The solids were filtered, rinsed with water (100 ml, pH 7.5), and filtered again. The solids were dried at 110° C. for 5 hours, then calcined in air from 110° C. to 425° C. in 5 hours and held at 425° C. for ere taken out of the oven, then returned to a 300° C. oven and heated in 1 hour to 425° C., then held at 425° C. for 2 hours to obtain the catalyst of the invention. Elemental analysis was: 3200 ppm Au; 1.47 percent Ti; 1550 ppm Na, 1.95 percent Ba. Oxidized gold comprised 42 weight percent of the total gold content, as measured by XPS. HR-TEM showed some metallic gold particles of average size 5.0 nm and many particles of about 1.5 nm.

The catalyst as evaluated in the hydro-oxidation of propylene to propylene oxide in the manner described in Example 1. The process was run for about 4 hours at 150° C.; then the catalyst was regenerated at 425° C. under a mixture of oxygen (20 volume percent) and water (1 volume percent), the balance being helium. After the first regeneration, the hydro-oxidation process was run at 150° C. for about 4 hours, and then the catalyst was regenerated a second time at 450° C. under the mixture of oxygen, water, and helium. After the second regeneration, the catalyst was evaluated in the hydro-oxidation process at 150° C. with the results shown in Table 4.

TABLE 4

Hydro-Oxidation of Propylene (PP) to Propylene Oxide (PO)[a]

| Temperature | Time on Stream (h) | Conv PP (mole %) | PO Sel (mole %) |
|---|---|---|---|
| 140 | 0.4 | 2.2 | 95 |
| 140 | 1.8 | 1.4 | 96 |
| 140 | 2.3 | 1.2 | 96 |
| Regenerate 425 | | | |
| 140 | 0.4 | 3.4 | 97 |
| 140 | 1.5 | 2.1 | 97 |
| 140 | 4.0 | 1.4 | 96 |
| Regenerate 450 | | | |
| 150 | 0.5 | 3.1 | 96 |
| 150 | 1.5 | 2.3 | 96 |
| 150 | 4.0 | 1.7 | 96 |

[a]Feedstream (mole percent): 20 percent propylene, 10 percent oxygen, 10 percent hydrogen, balance helium; 50° C., pressure atmospheric, GHSV 960 h$^{-1}$

EXAMPLE 17

A titanium-containing support was made by using silica powder (PQ-HP-420 silica; 50.0 g), which had been dried at 300° C. After cooling to room temperature, the silica powder was transferred in air to 2 L rotary evaporator flasks. The silica powder was gently rotated under vacuum on the rotary evaporator for 5 min. In a nitrogen dry box, tetrakis (trimethylsiloxy) titanium (Gelest, 2.60 g) were dissolved in isopropyl alcohol (300.0 g), and the resulting solution was transferred to an addition funnel and sealed. The tetrakis (trimethylsiloxy) titanium solution was added to the silica powder under vacuum, and the resulting mixture was kept under vacuum for an additional 5 min. Then, nitrogen was passed through the flask for about 16 hours. A vacuum was applied to remove solvent at 40° C. for 1 hour, then at 85° C. for 1 hour. The solids recovered were calcined in air in a muffle furnace from room temperature to 800° C. over 5 hours, then held at 800° C. for 5 hours, and cooled to room temperature to yield a titanium-containing support of the invention.

Chloroauric acid (0.150 g), lithium nitrate (0.160 g), and magnesium nitrate (0.30 g) were dissolved in deionized water (350 g). The resulting solution was heated to 70° C. while adjusting the pH to 7.8 dropwise with an aqueous solution of lithium carbonate (0.10 M). The resulting solution was cooled to room temperature; the pH rose to 8.3. Then, the titanium-containing support (5.0 g) was added to the solution. The flask was swirled on a circular shaker for 90 min while the pH was adjusted to 7.5 with an aqueous lithium carbonate solution (0.5 M). The solids were filtered using a Buchner funnel with Whatman paper #3. The solids were rinsed with water (40 mL, pH 7.00–8.00 made fresh with lithium carbonate), and rinsed again with methanol (80.0 mL). Filtering continued for min. The solids were put into a 60° C. vacuum oven for 3 hours to obtain a catalyst of this invention. The catalyst, white to pale blue in color, was not calcined, but was used after vacuum drying. Elemental analysis, by weight, was as follows: 0.037 percent Au, 0.56 percent Ti, 0.017 percent Na, 0.23 percent Mg, by NAA. The XPS showed 66 weight percent oxidized gold. Ti-XPS showed 92 percent low coordinate and 8 percent high coordinate titanium.

The catalyst (2.0 g) was evaluated in the hydro-oxidation of propylene to propylene oxide using the process conditions and with the results shown in Table 5.

TABLE 5

Hydro-oxidation of Propylene (PP) to Propylene Oxide (PO)[a,b]

| T, °C. | Time on Stream (h) | PP Conv, mole % | PO Sel, mole % | g PO/kg-cat-h | $H_2O$/PO |
|---|---|---|---|---|---|
| 180 | 9 | 0.90 | 88 | 26 | 3.8 |
| " | 18 | 1.06 | 89 | 32 | 3.4 |
| " | 36 | 1.20 | 91 | 36 | 3.0 |
| " | 72 | 1.40 | 91 | 41 | 3.0 |
| 190 | 80 | 1.57 | 89 | 46 | 3.4 |
| " | 110 | 1.55 | 89 | 46 | 3.3 |
| " | 168[b] | 1.24 | 90 | 112 | 2.7 |

[a]Except where otherwise noted, feedstream (mole percent) was: 20 percent propylene, 10 percent oxygen, 10 percent hydrogen, balance helium; Pressure atmospheric; GHSV 3000 h$^{-1}$.
[b]At 168 hours, feedstream (mole percent) was: 33 percent propylene, 10 percent oxygen, 10 percent hydrogen, balance helium; Pressure atmospheric; GHSV 6000 h$^{-1}$

EXAMPLE 18

A titanium-containing support (30 g) prepared as described in Example 7 was calcined in air at 575° C. for 8 hours and cooled to room temperature. A solution was prepared comprising chloroauric acid (0.035 g) and sodium acetate (0.5 g) in methanol (35 g). The sample was dried under vacuum at room temperature until free flowing, then heated under vacuum to 100° C. for 2 hours to yield a catalyst of this invention.

The catalyst (30 g) was evaluated in the hydro-oxidation of propylene to propylene oxide in the manner described in Example 1, with the exception that the total flow was 15.0 L/min; pressure was 210 psig (1448 kPa); and the shell temperature of the reactor was 160° C. A propylene conversion of 3.2 percent was obtained with a selectivity to propylene oxide of 96 percent.

EXAMPLE 19

Tetraethylorthosilicate (50 g) was cooled to under 5° C. in an ice-bath, and while stirring titanium (IV) tetra(ethoxide) (1.37 g) was added. To this cooled mixture, a cold (less than 5° C.) solution of tetrapropylammonium hydroxide (TPAOH, 43.9 g; 40 percent in water) and water (43.5 g) were added. After about 15 drops of the TPAOH/water mixture had been added while stirring, the solution was slightly cloudy. The remaining TPAOH/water mixture was then rapidly added to the TEOS/Ti mixture with vigorous stirring over a period of 5 min, and shortly thereafter the solution became clear indicating the apparent absence of a solid phase. Stirring was continued until the mixture's temperature was that of room temperature, and then the mixture was hydrolyzed at room temperature on a gyrotary shaker for 24 hours. The hydrolyzed suspension was then heated at 95° C. for 64 hours. Following crystallization, the suspension was centrifuged at 16,400 rpm for 2 hours, and a solid phase was recovered by decanting the liquor. The solid phase was redispersed in fresh water, and the suspension was centrifuged as described above. This rinsing process was repeated 3 times. The resulting purified suspension was freeze dried to obtain a powder, which was identified by XRD to be a titanosilicate of MFI structure. Crystal size was on average 40–60 nm. XPS showed peaks at 460 eV and 458 eV, attributed to framework and grafted titanium, respectively.

What is claimed is:

1. A process of preparing an olefin oxide comprising contacting an olefin having at least three carbon atoms with oxygen in the presence of hydrogen and an optional diluent, and in the presence of a catalyst comprising oxidized gold on a titanium-containing support.

2. The process of claim 1 wherein the olefin is a $C_{3-12}$ monoolefin or diolefin.

3. The process of claim 1 wherein the olefin is selected from propylene, butadiene, cyclopentadiene, dicyclopentadiene, styrene, α-methylstyrene, divinylbenzene, allyl alcohol, diallyl ether, allyl ethyl ether, allyl butyrate, allyl acetate, allyl benzene, allyl phenyl ether, allyl propyl ether, allyl anisole, and mixtures thereof.

4. The process of claim 3 wherein the olefin is propylene.

5. The process of claim 1 wherein the olefin is used in a quantity greater than 1 and less than 99 mole percent, based on the total moles of olefin, oxygen, hydrogen, and optional diluent.

6. The process of claim 1 wherein the oxygen is used in a quantity greater than 0.01 and less than 30 mole percent, based on the total moles of olefin, oxygen, hydrogen, and optional diluent.

7. The process of claim 1 wherein the hydrogen is used in a quantity greater than 0.01 and less than 50 mole percent, based on the total moles of olefin, oxygen, hydrogen, and optional diluent.

8. The process of claim 1 wherein a diluent is employed.

9. The process of claim 8 wherein when the process is conducted in a vapor phase, the diluent is selected from the group consisting of helium, nitrogen, argon, methane, carbon dioxide, steam, and mixtures thereof; and wherein when the process is conducted in a liquid phase, the diluent is selected from $C_{6-15}$ aromatic hydrocarbons, chlorinated $C_{1-10}$ hydrocarbons, $C_{1-10}$ aliphatic alcohols, chlorinated $C_{1-10}$ alkanols, $C_{2-20}$ ethers, and liquid polyethers, polyalcohols, and polyesters.

10. The process of claim 1 wherein a diluent is used in a gas phase in a quantity greater than 0 and less than 90 mole percent, based on the total moles of olefin, oxygen, hydrogen, and optional diluent; and/or wherein a liquid diluent (or solvent) is used in a liquid phase in a quantity greater than 5 and less than 95 weight percent, based on the combined weight of the olefin and the diluent.

11. The process of claim 1 wherein high resolution transmission electron microscopy and/or Mie scattering is employed to analyze for metallic gold.

12. The process of claim 1 wherein the gold is loaded onto the support in an amount greater than 0.001 and less than 20 weight percent, based on the total weight of the catalyst.

13. The process of claim 12 wherein the gold loading is greater than 0.001 and less than 0.5 weight percent, based on the total weight of the catalyst.

14. The process of claim 13 wherein the gold loading is greater than 0.005 and less than 0.1 weight percent, based on the total weight of the catalyst.

15. The process of claim 1 wherein greater than 30 weight percent of the total gold present in the catalyst is oxidized gold.

16. The process of claim 1 wherein greater than 50 weight percent of the total gold present in the catalyst is oxidized gold.

17. The process of claim 1 wherein greater than 70 weight percent of the total gold present in the catalyst is oxidized gold.

18. The process of claim 1 wherein greater than 90 weight percent of the total gold present in the catalyst is oxidized gold.

19. The process of claim 1 wherein the titanium-containing support comprises a titanosilicate.

20. The process of claim 19 wherein the silicon to titanium atomic ratio in the titanosilicate support ranges from 1:1 to 500:1.

21. The process of claim 19 wherein the titanosilicate has an MFI crystalline structure and contains a plurality of titanium coordination environments.

22. The process of claim 21 wherein the titanosilicate comprises at least one framework (low coordinate) titanium species and at least one grafted (high coordinate) titanium species.

23. The process of claim 1 wherein the titanium-containing support comprises titanium dispersed on silica.

24. The process of claim 23 wherein the titanium-containing support comprises a plurality of titanium coordination environments.

25. The process of claim 23 wherein a titanium silsesquioxane complex or mixture of said complexes is dispersed on silica.

26. The process of claim 23 wherein the titanium dispersed on silica is prepared by dispersing a mixture of titanium alkoxide and promoter metal alkoxide on a silica support and thereafter calcining the support.

27. The process of claim 23 wherein the titanium dispersed on silica is prepared by dispersing a titanium-containing monomer, dimer, polymer or mixture thereof on a silica support and thereafter calcining the support.

28. The process of claim 27 wherein the titanium-containing monomer, dimer, or polymer is a titanosiloxane monomer, dimer, or polymer.

29. The process of claim 28 wherein the titanosiloxane monomer is represented by the following formula:

wherein $R^1$, $R^2$, and $R^3$ are each independently selected from the group consisting of alkyl, alkoxy, aryl, aryloxy, and halo moieties; x is an integer ranging from 0 to 3; and y is an integer ranging from 0 to 3; and wherein the titanosiloxane dimer and polymer may be represented by the formula shown hereinabove, with the exception that $R^3$ can also be a repeating unit selected from the following:

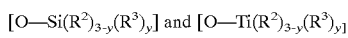

wherein $R^2$, $R^3$, and y are any of the moieties defined hereinbefore.

30. The process of claim 29 wherein the titanosiloxane monomer is selected from tetrakis(trimethylsiloxy)titanium, tetrakis(triethylsiloxy)titanium, tetrakis(triethoxysiloxy)titanium, and tetrakis[tris(tert-butoxy)siloxy]titanium.

31. The process of claim 29 wherein the titanosiloxane polymer is selected from diethoxysiloxane-ethyltitanate copolymer.

32. The process of claim 27 wherein the titanium-containing polymer is an organic titanium-containing polymer comprised of a backbone of titanium, silicon, and —(CR$_2$)$_z$ groups, wherein z ranges from 1 to about 20, and each R is independently selected from alkyl, aryl, alkoxy, or halide.

33. The process of claim 1 wherein the titanium-containing support is selected from titanium oxides, promoter metal titanates, and titanium dispersed on promoter metal silicates.

34. The process of claim 1 wherein the titanium loading is greater than about 0.02 weight percent and less than about 20 weight percent, based on the weight of the support.

35. The process of claim 1 wherein the catalyst is bound to a second support.

36. The process of claim 35 wherein the second support is selected from silicas, aluminosilicates, titania, magnesia, carbon and mixtures thereof.

37. The process of claim 1 wherein the catalyst is in the form of a bead, pellet, sphere, honeycomb, monolith, extrudate, or film, or wherein the catalyst is supported on a second support which is in the form of a bead, pellet, sphere, honeycomb, monolith, extrudate, or film.

38. The process of claim 1 wherein the catalyst further comprises at least one promoter.

39. The process of claim 38 wherein the promoter is selected from silver, Group 1, Group 2, the lanthanide rare earth and actinide elements, and combinations thereof.

40. The process of claim 38 wherein the promoter is selected from silver, magnesium, calcium, barium, lithium, sodium, potassium, rubidium, cesium, erbium, lutetium, and combinations thereof.

41. The process of claim 1 wherein the process is conducted at a temperature greater than 20° C. and less than 300° C.

42. The process of claim 1 wherein the process is conducted at a temperature greater than 130° C. and less than 300° C.

43. The process of claim 1 wherein the process is conducted at a pressure between atmospheric and 400 psig (2758 kPa).

44. The process of claim 1 wherein the process is conducted in a gaseous phase at a gas hourly space velocity of the olefin greater than 10 h$^{-1}$ and less than 50,000 h$^{-1}$.

45. The process of claim 1 wherein the process is conducted in a liquid phase at a weight hourly space velocity of the olefin greater than 0.01 h$^{-1}$ and less than 100 h$^{-1}$.

46. The process of claim 1 wherein the process is conducted in a reactor selected from batch, fixed bed, transport bed, moving bed, fluidized bed, trickle bed, shell and tube, continuous flow, intermittent flow, and swing reactors.

47. The process of claim 1 wherein the process exhibits an olefin conversion of greater than 0.50 mole percent and a selectivity to olefin oxide of greater than 70 mole percent.

48. The process of claim 1 wherein the process exhibits an olefin conversion of greater than 1.5 mole percent and a selectivity to olefin oxide of greater than 90 mole percent.

49. The process of claim 1 wherein the catalyst is active for at least 100 hours.

50. The process of claim 1 wherein the catalyst is active for at least 400 hours.

51. A process of preparing propylene oxide comprising contacting in a gas phase propylene with oxygen in the presence of hydrogen and an optional diluent and in the presence of a catalyst containing oxidized gold on a titanium-containing support.

52. The process of claim 51 wherein the quantity of propylene is greater than 20 and less than 70 mole percent, based on the total moles of propylene, oxygen, hydrogen, and optional diluent.

53. The process of claim 51 wherein the quantity of oxygen is greater than 5 and less than 20 mole percent, based on the total moles of propylene, oxygen, hydrogen, and optional diluent.

54. The process of claim 51 wherein the quantity of hydrogen is greater than 3 and less than 20 mole percent, based on the total moles of propylene, oxygen, hydrogen, and optional diluent.

55. The process of claim 51 wherein the quantity of diluent is greater than 15 and less than 70 mole percent, based on the total moles of propylene, oxygen, hydrogen, and optional diluent.

56. The process of claim 51 wherein the process achieves a selectivity to propylene oxide of greater than 90 mole percent.

57. The process of claim 51 wherein the process achieves a propylene conversion of greater than 2.0 mole percent.

58. The process of claim 51 wherein the productivity to propylene oxide is greater than 50 grams propylene oxide per kilogram catalyst per hour.

59. A composition comprising oxidized gold on a titanium-containing support.

60. The composition of claim 59, having the proviso that the composition excludes oxidized gold on bulk titanium dioxide.

61. The composition of claim 59 wherein the gold loading is greater than 0.001 and less than 20 weight percent, based on the total weight of the catalyst.

62. The composition of claim 59 wherein the gold loading is greater than 0.005 and less than 0.5 weight percent, based on the total weight of the catalyst.

63. The composition of claim 59 wherein the gold loading is greater than 0.005 and less than 0.1 weight percent, based on the total weight of the catalyst.

64. The composition of claim 59 wherein greater than 30 weight percent of the gold in the catalyst is oxidized gold.

65. The composition of claim 59 wherein greater than 50 weight percent of the gold in the catalyst is oxidized gold.

66. The composition of claim 59 wherein greater than 70 weight percent of the gold in the catalyst is oxidized gold.

67. The composition of claim 59 wherein greater than 90 weight percent of the gold in the catalyst is oxidized gold.

68. The composition of claim 59 wherein if gold particles are present, the particles have an average size less than 1 nm.

69. The composition of claim 59 wherein the catalyst further comprises at least one promoter.

70. The composition of claim 69 wherein the promoter is selected from silver, Group 1, Group 2, the lanthanide rare earth and actinide elements, and combinations thereof.

71. The composition of claim 69 wherein the promoter is selected from silver, agnesium, calcium, barium, lithium, sodium, potassium, rubidium, cesium, erbium, lutetium, and combinations thereof.

72. The composition of claim 69 wherein the total concentration of promoter(s) is greater than about 0.01 and less than about 20 weight percent, based on the total weight of the catalyst.

73. The composition of claim 59 wherein the titanium-containing support is a titanosilicate.

74. The composition of claim 73 wherein the silicon to titanium ratio ranges from 1:1 to 500:1.

75. The composition of claim 73 wherein the titanosilicate has an MFI crystalline structure and contains a plurality of titanium coordination environments.

76. The composition of claim 75 wherein at least one titanium species is a framework (low coordinate) species and at least one titanium species is a grafted (high coordinate) species.

77. The composition of claim 59 wherein the titanium-containing support comprises titanium dispersed on silica.

78. The composition of claim 77 wherein the support is prepared by dispersing a titanium silsesquioxane complex or combination thereof onto a silica support.

79. The composition of claim 78 wherein the support is prepared by dispersing a mixture of titanium and promoter metal alkoxides on a silica support and thereafter calcining the support.

80. The composition of claim 79 wherein the support is prepared by dispersing a titanium-containing monomer, dimer, or polymer onto a silica support and thereafter calcining the support.

81. The composition of claim 80 wherein the titanium-containing monomer, dimer, or polymer is a titanosiloxane monomer or polymer.

82. The composition of claim 81 wherein the titanosiloxane monomer is represented by the following formula:

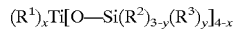

wherein $R^1$, $R^2$, and $R^3$ are each independently selected from the group consisting of alkyl, alkoxy, aryl, aryloxy, and halo moieties; x is an integer ranging from 0 to 3; and y is an integer ranging from 0 to 3; and wherein the titanosiloxane dimer or polymer is represented by the formula shown hereinabove, with the exception that $R^3$ may also be a repeating unit selected from the following moieties:

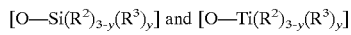

wherein $R^2$, $R^3$, and y can be selected from any of the species defined hereinbefore.

83. The composition of claim 81 wherein the titanium containing polymer is comprised of a backbone of titanium, silicon, and —$(CR_2)_z$— moieties, wherein z is an integer ranging from 1 to about 20 and wherein each R is independently selected from alkyl, aryl, alkoxy, and halide groups.

84. The composition of claim 59 wherein the titanium-containing support is selected from titanium oxides, promoter metal titanates, and titanium dispersed on promoter metal silicates.

85. The composition of claim 59 wherein the titanium loading is greater than 0.02 and less than 20 weight percent, based on the weight of the support.

86. The composition of claim 59 wherein the composition is extruded with, bound to or supported on a second support.

87. The composition of claim 86 wherein the second support is selected from silicas, aluminas, aluminosilicates, magnesia, titania, carbon, and mixtures thereof.

88. The composition of claim 87 wherein the quantity of second support ranges from 0 to 95 weight percent, based on the combined weight of the catalyst and second support.

89. The composition of claim 59 wherein the catalyst is in the form of a bead, pellet, sphere, honeycomb, monolith, extrudate, or film, or wherein the catalyst is supported on a second support which is in the form of a bead, pellet, sphere, honeycomb, monolith, extrudate, or film.

90. The composition of claim 59 wherein the catalyst is prepared by a method comprising dispersing by impregnation or deposition precipitation a gold compound comprising oxidized gold onto a titanium-containing support under conditions sufficient to minimize the reduction of oxidized gold to metallic gold.

91. The composition of claim 90 wherein a solution containing a promoter is dispersed onto the support, or an anionic additive is dispersed onto the support, or a combination of promoter(s) and anionic additive(s) is dispersed onto the support.

92. The composition of claim 91 wherein the additives are selected from the group consisting of promoter metal halides, phosphates, sulphates, borates, carbonates, and carboxylates.

93. The composition of claim 92 wherein an aqueous solution having a pH between 7 and 14 is used for impregnation or deposition precipitation.

94. The composition of claim 92 wherein an organic solvent is used in the impregnation or deposition precipitation.

95. A method of preparing the catalyst of claim 59 comprising dispersing by impregnation or deposition precipitation a gold compound comprising oxidized gold onto a titanium-containing support under conditions sufficient to minimize the reduction of oxidized gold to metallic gold.

96. The method of claim 95 wherein one or more anionic additives are dispersed onto the support, or a combination of promoter(s) and anionic additive(s) is dispersed onto the support.

97. The method of claim 96 wherein an aqueous solution having a pH between about 7 and about 14 is used.

98. The method of claim 96 wherein an organic solvent is used.

99. A composition comprising a titanium-containing support characterized by a plurality of titanium coordination environments.

100. The composition of claim 99 wherein one titanium coordination environment is a framework (low coordination) site and one titanium coordination environment is a non-framework (high coordination) site.

101. The composition of claim 100 wherein the titanium-containing support is a titanosilicate characterized by an MFI crystallographic structure.

102. The composition of claim 99 wherein the support is prepared by a method comprising dispersing a titanium-containing monomer, dimer, or polymer onto a silica support and thereafter calcining the support.

103. The composition of claim 102 wherein the titanium-containing monomer, dimer, or polymer is a titanosiloxane monomer or polymer.

104. The composition of claim 103 wherein the titanosiloxane monomer is represented by the following formula:

$$(R^1)_x Ti[O-Si(R^2)_{3-y}(R^3)_y]_{4-x}$$

wherein $R^1$, $R^2$, and $R^3$ are each independently selected from the group consisting of alkyl, alkoxy, aryl, aryloxy, and halo moieties; x is an integer ranging from 0 to 3; and y is an integer ranging from 0 to 3; and wherein the titanosiloxane dimer or polymer is represented by the formula shown hereinabove, with the exception that $R^3$ may also be a repeating unit selected from the following moieties:

$$[O-Si(R^2)_{-y}(R^3)_y] \text{ and } [O-Ti(R^2)_{3-y}(R^3)_y]$$

wherein $R^2$, $R^3$, and y can be selected from any of the species defined hereinbefore.

* * * * *